US012571023B2

(12) United States Patent
Hanna et al.

(10) Patent No.: US 12,571,023 B2
(45) Date of Patent: Mar. 10, 2026

(54) COMPOSITION AND METHODS FOR AFFINITY DIRECTED ENRICHMENT OF RARE SPECIES

(71) Applicant: CY Molecular Diagnostics, Inc., San Diego, CA (US)

(72) Inventors: William L. Hanna, San Diego, CA (US); Alexander Yum, San Diego, CA (US)

(73) Assignee: Spark Molecular Diagnostics, Inc., San Diego, CA (US)

( * ) Notice: Subject to any disclaimer, the term of this patent is extended or adjusted under 35 U.S.C. 154(b) by 603 days.

(21) Appl. No.: 16/975,634

(22) PCT Filed: Feb. 26, 2019

(86) PCT No.: PCT/US2019/019665
§ 371 (c)(1),
(2) Date: Aug. 25, 2020

(87) PCT Pub. No.: WO2019/165469
PCT Pub. Date: Aug. 29, 2019

(65) Prior Publication Data
US 2020/0399683 A1      Dec. 24, 2020

Related U.S. Application Data

(60) Provisional application No. 62/635,257, filed on Feb. 26, 2018.

(51) Int. Cl.
C12Q 1/6806      (2018.01)
C12Q 1/6827      (2018.01)
(52) U.S. Cl.
CPC ......... *C12Q 1/6806* (2013.01); *C12Q 1/6827* (2013.01)
(58) Field of Classification Search
CPC . C12Q 1/6827; C12Q 1/6806; C12N 15/1093
See application file for complete search history.

(56) References Cited

U.S. PATENT DOCUMENTS

| | | |
|---|---|---|
| 4,876,187 A | 10/1989 | Duck |
| 5,660,988 A | 8/1997 | Duck |
| 5,731,146 A * | 3/1998 | Duck ................... C12Q 1/6823 |
| | | 435/6.12 |
| 6,274,316 B1 | 8/2001 | Modrusan |
| 2004/0248150 A1 | 12/2004 | Singh |
| 2015/0072872 A1* | 3/2015 | Rabinowitz ............ G16H 50/30 |
| | | 702/19 |

OTHER PUBLICATIONS

Nelson et al., "Detection of all single-base mismatches in solution by chemiluminescence", Nucleic Acid Research, 1996, vol. 24(24) :4998-5003 (Year: 1996).*
Lou et al., "Detection of rare mutant K-ras DNA in a single-tube reaction using peptide nucleic acid as both PCR clamp and sensor probe", Nucleic Acid Research, 2006, vol. 34(2):1-7 (Year: 2006).*
Scorilas et al., "Novel biotinylated acridinium derivatives: New reagents for fluorescence immunoassays and proteomics", Clinica Chimica Acta, 2005, vol. 357: 159-167. (Year: 2005).*
Goto et al., "Single-nucleotide polymorphism analysis by hybridization protection assay on solid support", Analytical Biochemistry. 2002, vol. 307: 25-32 (Year: 2002).*
Pringle "Acridinium Ester Labels: Esters, Sulfonamides, and Their Applications" Journal of Clinical Ligand Assay (1999) 22: 105-122 . (Year: 1999).*
International Search Report dated Jun. 17, 2019, for related PCT application serial No. PCT/2019/019665, filed on Feb. 26, 2019.

* cited by examiner

*Primary Examiner* — Nancy J Leith
(74) *Attorney, Agent, or Firm* — Fish IP Law, LLP

(57) ABSTRACT

Compositions and methods for the selective extraction of rare molecular species from a mixture containing a predominance of related molecular species, and their subsequent release are provided. Compositions include a segregating probe having a target-specific targeting portion, a protecting portion, a scissile or cleavable site or portion, and a capture portion. Complex formation between the targeting portion and the target rare species results in protection of the cleavable site. Such complexes remain intact through a cleavage step directed to the cleavable site or portion of the segregating probe. While complex formation can occur between a segregating probe and a related, but non-target, species the cleavable site is not protected in such complexes. A subsequent capture step directed to the capture portion selectively captures or segregates the target rare species from the general milieu, which can be removed by washing. Subsequent release of the target rare species from the segregating probe provides a solution enriched in the target rare species.

14 Claims, 27 Drawing Sheets

Specification includes a Sequence Listing.

Structures of Designed Biotinyl Acridinium NHS Ester

Synthesis of Quarternary N-10-Biotinyl Acridinium NHS Ester

KRAS WT (SEQ ID NO 1)

KRAS WT (SEQ ID NO 1) AFTER ENRICHMENT

COMPOSITION AND METHODS FOR AFFINITY DIRECTED ENRICHMENT OF RARE SPECIES

This application claims the benefit of U.S. Provisional Application No. 62/635,257, filed on Feb. 26, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is isolation or enrichment of rare molecular species from a mixture, in particular nucleic acids.

BACKGROUND

The background description includes information that may be useful in understanding the present invention. It is not an admission that any of the information provided herein is prior art or relevant to the presently claimed invention, or that any publication specifically or implicitly referenced is prior art.

Rare polynucleotide targets, such as mutated DNA found in cancer cells or any target genes that are found in a specimen, and blood occur in a milieu in which the vast majority of polynucleotide targets represent the sequence of wild-type genes. Many of these rare polynucleotide targets have sequences that are nearly identical to the wild-type sequence, and are not readily distinguishable from them using conventional hybridization-based approaches (such as PCR). For example, if such a rare polynucleotide target has a single nucleotide change (e.g. a SNP) or small (i.e. 20 nucleotides or less) insertion or deletion it is very difficult to isolate or identify from a mixture containing a large excess of the wild-type polynucleotide (for example, in plasma or a tissue specimen).

The separation of polynucleotides carrying cancer-related mutations or rare nucleic acids (for instance from 0.1% to 1%) from tissue specimens or blood plasma (which can contain 99.0-99.9% or more of the corresponding wild-type sequence) is an extremely complex task. For example, United States Patent Application Publication No. 2008/0194414, to Albert et al, describes the use of immobilized oligonucleotide probes to selectively capture polynucleotide fragments generated from genomic DNA in order to reduce the complexity of the resulting polynucleotide mixture. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. It is doubtful, however, that such an approach can adequately distinguish between a rare DNA target sequence containing a single nucleotide difference and a corresponding wild type sequence present in vast excess as factors such as partial sequence overlap and high G/C content can interfere with selectivity.

In another approach, described in United States Patent Application No. 2015/0072872, to Rabinowitz, fetal chromosomal DNA can be separated from parental chromosomal DNA (which is similar, and present in large excess) by selectively enriching the fetal DNA through capture using a plurality of polymorphic loci. Such an approach, however, is not readily applied to identification of a specific rare gene sequence carrying a single nucleotide polymorphism.

In another approach, as described in United States Patent Application No. 2016/0304954, to Shengrong, mutant sequences occurring at low frequency against a background of wild type polynucleotides are identified by circularizing the population of polynucleotides, amplifying the circularized polynucleotides, and sequencing the amplified polynucleotides. Comparison of the sequences can be used to identify the sequence variant. Such an approach, however, is very time and equipment intensive, and is necessarily limited to sequences that are readily circularized. In addition, it is not clear how infrequently a rare mutant sequence can occur and still be readily identifiable by such an approach.

In still another approach, as described in United States Patent Application Publication No. 2017/0029875 (to Zhang and Wang), rare alleles that are very similar to wild type alleles that are present in excess are selectively identified using a pair of nucleic acid probes. One of these (the "Probe") is complementary to the rare allele whereas the remaining probe (the "Sink") is complementary to the wild-type sequence and is present in excess. Competition between the nucleic acid probes functionally improves the specificity of the "Probe" for the rare allele by rendering the large excess of wild-type allele nucleic acid unavailable for hybridization. This approach, however, is not generally applicable and may prove challenging for longer sequences and those with high G/C ratios.

United States Patent Application Publication No. 2017/005134, to Vogelstein et al., describes a method in which a large number of unique sequence identifiers are grafted onto a smaller population of analyte nucleic acid sequences, followed by massively parallel sequencing. Subsequent statistical analysis generates families composed of different unique identifiers coupled to identical or similar analyte nucleic acid sequences. If all the members of such a family include a mutation the mutation is considered to be part of the original analyte nucleic acid sequence; if all the members do not show the mutation it is considered to be an artifact of amplification. This improved distinction between mutation and amplification artifact can improve the fidelity of identification of rare mutations.

Thus, there is still a need for effective method of selecting rare target species from a milieu containing a large excess of similar species.

SUMMARY OF THE INVENTION

The inventive subject matter provides compositions and methods for the selective extraction of rare molecular species from a mixture containing a predominance of related molecular species, and their subsequent release. Compositions include a segregating probe having a target-specific targeting portion, a protecting portion, a scissile or cleavable site or portion, and a capture portion. Complex formation between the targeting portion and the target rare species results in protection of the cleavable site. Such complexes remain intact through a cleavage step directed to the cleavable site or portion of the segregating probe. While complex formation can occur between a segregating probe and a related, but non-target, species the cleavable site is not protected in such complexes. A subsequent capture step directed to the capture portion selectively captures or segregates the target rare species from the general milieu, which can be removed by washing. Subsequent release of the target rare species from the segregating probe provides a solution enriched in the target rare species.

One embodiment of the inventive concept is a method for segregating rare species by contacting a segregating probe with a sample that includes a mixture of a rare species and a related common species to form a first reaction mixture, where the common species is present in at least a 5-fold molar excess over the rare species. In some embodiments the rare species and the common species are polynucleotides, and the rare species can differ from the common species by from 1 to 20 nucleotides. A first complex is formed that includes the segregating probe and the rare species and a plurality of second complexes are formed that include the segregating probe and the common species in a first reaction mixture. The first reaction mixture is then contacted with a cleavage reagent to form a second reaction mixture. The addition of the cleavage reagent results in cleavage of a scissile bond of the segregating probe of the plurality of second complexes while leaving the scissile bond of the segregating probe of the first complex intact. The second reaction mixture is then contacted with a capture species to form a third complex that includes the capture species and the first complex, permitting segregating and/or separation of the second complex from the third complex (which includes the rare species). The rare species can subsequently be released from the third complex following segregation. In some embodiments the rare species can be amplified (for example, by PCR) following segregation from the common species.

In such a method the segregating probe includes a targeting moiety capable of forming a complex with either or both of the rare species and the common species, a capture tag capable of forming a complex with the capture species, and a scissile bond positioned between the targeting moiety and the capture tag. Suitable targeting moieties include polynucleotides, and antibodies, an antibody fragments, and antibody derivatives. Suitable scissile bonds include carbonyl esters and sulfonamide esters. Suitable capture tags include biotin, iminobiotin, digoxigenin, polynucleotides, polypeptides, polyhistidine, antibodies, antibody fragments, and/or antibody derivatives. Accordingly, such a method can utilize avidin, streptavidin, antibodies, antibody fragments, antibody derivatives, nickel complexes, and/or polynucleotides as capture species. In order to facilitate handling such capture species further include a particle, a magnetically responsive particle, a membrane, a well of a microwell plate, an interior surface of a pipette tip or vial, and/or a filter.

Another embodiment of the inventive concept is a segregating probe that includes a targeting moiety that is selected to form a complex with rare species and a common species, a capture tag, a scissile bond positioned between the targeting moiety and the capture tag, and a protective group. The protective group is selected to provide a reduced rate of cleavage of the scissile bond in complexes where the segregating probe is complexed with the rare species relative to the rate of cleavage of the scissile bond in complexes where the segregating probe is complexed with the common species. In some embodiments the rare species and the common species are polynucleotides, which can differ by from 1 to 20 nucleotides. Suitable targeting moieties include polynucleotides, antibodies, antibody fragments, and/or antibody derivatives. Suitable scissile bonds include carbonyl esters and/or sulfonamide esters. Suitable capture tags include biotin, iminobiotin, digoxigenin, polynucleotides, polypeptides, polyhistidine, antibodies, antibody fragments, and/or antibody derivatives. Such capture tags can be selected to form a complex with a capture species, such as avidin, streptavidin, an antibody, an antibody fragment, an antibody derivative, a nickel complex, and/or a polynucleotide. Such capture species can also include a particle, a magnetically responsive particle, a membrane, a well of a microwell plate, an interior surface of a pipette tip or vial, and/or a filter.

Another embodiment of the inventive concept is an intermediate useful for preparing a segregating probe of the inventive concept. Such an intermediate includes a reactive group that is selected to couple to a targeting moiety, where the targeting moiety is selected to form a complex with rare species and a common species. Such an intermediate also includes a capture tag, a scissile or cleavable bond or moiety positioned between the reactive group and the capture tag, and a protective group. The protective group is selected to provide a reduced rate of cleavage of the scissile bond in complexes that include the segregating probe and the rare species relative to the rate of cleavage of the scissile bond in complexes comprising that include the segregating probe and the common species. In some embodiments such rare species and common species are polynucleotides, which can differ by from 1 to 20 nucleotides. Suitable targeting moieties include polynucleotides, antibodies, antibody fragments, and/or antibody derivatives. Suitable scissile bonds include carbonyl esters and/or sulfonamide esters. Suitable capture tags include biotin, iminobiotin, digoxigenin, polynucleotides, polypeptides, polyhistidine, antibodies, antibody fragments, and antibody derivatives. Such capture tags can be selected to form a complex with a capture species such as avidin, streptavidin, an antibody, an antibody fragment, an antibody derivative, a nickel complex, and a polynucleotide. Such capture species can also include a particle, a magnetically responsive particle, a membrane, a well of a microwell plate, an interior surface of a pipette tip or vial, and/or a filter. Suitable reactive include carboxylic acids, carboxylic acid esters, aldehydes, epoxides, cyanogen halides, dichlorotriazine, and hydrazides.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 depicts various embodiments of a segregating probe of the inventive concept.

FIG. 2A schematically depicts the lack of segregation of a non-target species on utilization of a segregating probe of the inventive concept.

FIG. 2B schematically depicts the segregation of a target species on utilization of a segregating probe of the inventive concept.

FIG. 3A schematically depicts interactions of a segregating probe of the inventive concept with a mixture non-target species and rare target species.

FIG. 3B schematically depicts differential cleavage of a bound/hybridized segregating probe of the inventive concept to release non-target species.

FIG. 3C schematically depicts removal of the non-target species following cleavage of a segregating probe of the inventive concept.

FIG. 3D schematically depicts release of the target species to generate a rare target-enriched preparation.

FIG. 4: FIG. 4 depicts an example of a base-sensitive linkers. The reaction begins with the attack by mild alkaline sodium borate anions on target segregating probe compound. Under alkaline conditions an alcohol intermediate is formed, followed by rapid conversion to an excited X-ketone compound. This reaction cleaves unbound target segregating probes to leave only bound duplexes of target segregating probe and rare nucleic acids that are protected by hybridization target segregating probe.

FIG. 5 depicts structures of two exemplary dye esters are used as target captures, where dye accesses cleavage on the carboxylate ester, and sulfonamide ester, assisted by a phenyl leaving group. L1, L2, and L3 can be electron donors (such as methyl, fluoride, bromide, and/or chloride) and L4 can include one, two, or more carbons. L1, L2, L3, and L4 can include a linker, which links to a capture moiety (such as biotin or a biotin-like compound) used for binding to a protein or other capturing species on magnetic beads.

FIG. 6: FIG. 6 depicts structures of N-Phthalimidyl-oxycarbonyl related compounds, (see EP1646,609B1) as used as a target capture for enhancement of purity of rare nucleic acids.

FIG. 7: Alternative intermediate compounds.

FIG. 9: Exemplary structures of X, Y, Z chemical groups useful for segregating probe intermediates.

FIG. 10: FIG. 10 depicts cleavage of segregating probes of the inventive concept by hydrolysis. The ester can be cleaved using an alkaline buffer. The mechanism is shown for two hydrolysis pathways. The fast, nonselective reaction using hydrogen peroxide cleaves all esters, whereas the mild reaction using sodium borate buffer at about pH 8, cleaves esters selectively.

FIG. 11 schematically depicts isolation of rare nucleic acid using a method of the inventive concept. Left hand-side: Matched hybridization of the segregating probe with the target rare nucleic acid, containing four blocks: L1, or L2, X, Y, and Z, remains intact following the cleavage reaction. Right hand-side: Mismatched segregating probe with wild-type sequence loses three components (L1 or L2, X, Y) on cleavage. The binding moiety (e.g. biotin) is lost, and only the leaving group and linker remains is such a duplex.

FIG. 12: The structures of two TCMs, Biotin Acridinium NHS-Ester, and Biotin Acridinium Sulfonamide NHS-Ester.

FIG. 13 shows the structures of two segregating probe intermediates based on biotinyl dye NHS esters contain three chemical building blocks. Each have specific functions in a sample preparation process based on a segregating probe produced using such intermediates. The ester linkage of such molecules can be stable under the cleavage by mild sodium borate buffer pH 8, when hybridized to a target rare polynucleotide.

FIG. 14: 2-Biotinyl Dye NHS Ester is synthesized as shown.

FIG. 15: First portion of a synthesis of compound 17, in which biotin is quarternized to 10-nitrogen position of the dye.

FIG. 16: Second portion of a synthesis of compound 17, in which the quaternary N-10-Biotinyl Dye NHS Ester is synthesized.

FIG. 17 shows a synthetic route for a segregating probe intermediate (compound 25) of the inventive concept, with a terminal N-hydroxysuccinimide group suitable for coupling the amine groups.

FIG. 18A shows the results of Sanger sequencing of a preparation of KRAS wild type (WT) sequence (SEQ ID NO 1) containing 5% KRAS G12A mutation (SEQ ID NO 2) prior to treatment using a segregating probe of the inventive concept. Base identification was automated and provided by commercial software. FIG. 18B shows the results of Sanger sequencing of a preparation of KRAS wild type (WT) sequence (SEQ ID NO 1) containing 5% KRAS G12A mutation (SEQ ID NO 2) following treatment using a segregating probe of the inventive concept. Enrichment of the KRAS G12A mutation sequence (SEQ ID NO 2) is evident. Base identification was automated and provided by commercial software.

FIG. 19A shows the results of Sanger sequencing of a preparation of KRAS wild type (WT) sequence (SEQ ID NO 1) containing 20% KRAS G12A mutation (SEQ ID NO 2) prior to treatment using a segregating probe of the inventive concept. Base identification was automated and provided by commercial software. FIG. 19B shows the results of Sanger sequencing of a preparation of KRAS wild type (WT) sequence (SEQ ID NO 1) containing 20% KRAS G12A mutation (SEQ ID NO 2) following treatment using a segregating probe of the inventive concept. Enrichment of the KRAS G12A mutation sequence (SEQ ID NO 2) is evident. Base identification was automated and provided by commercial software.

FIG. 20A shows the results of Sanger sequencing of a preparation of KRAS wild type (WT) sequence (SEQ ID NO 1) prior to treatment using a segregating probe of the inventive concept. Base identification was automated and provided by commercial software. FIG. 20B shows the results of Sanger sequencing of a preparation of KRAS wild type (WT) sequence (SEQ ID NO 1) following treatment using a segregating probe of the inventive concept directed to KRAS G12A mutation (SEQ ID NO 2). There is no evidence of the KRAS G12A mutation sequence (SEQ ID NO 2), indicating that the enrichment reaction is template dependent and is not an artifact of the segregation process. Base identification was automated and provided by commercial software.

DETAILED DESCRIPTION

Figure 1:
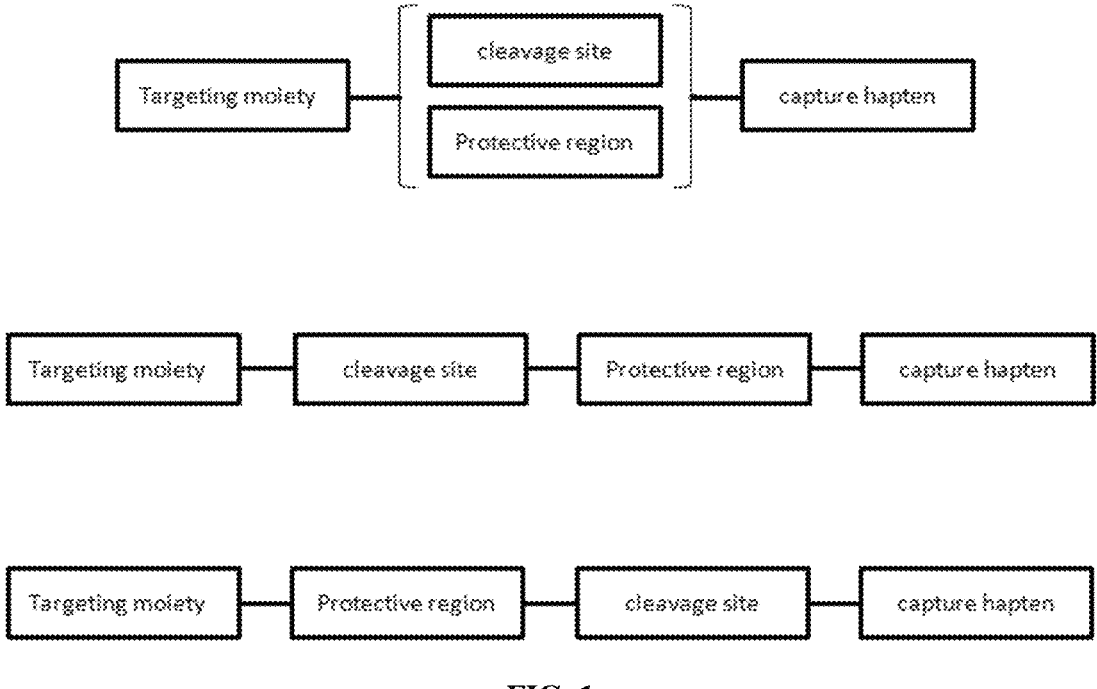
FIG. 1.

The following description includes information that may be useful in understanding the present invention. It is not an admission that any of the information provided herein is prior art or relevant to the presently claimed invention, or that any publication specifically or implicitly referenced is prior art.

The inventive subject matter provides compositions and methods in which a molecular species that occurs at low frequency in a solution (for example, representing less than about 20%, less than about 10%, less than 8%, less than 6%, less than 5%, less than 4%, less than 3%, less than 2%, less than 1%, and/or less than 0.5% of molecules of a similar type in solution) can be segregated from a mixture of such molecules in solution. For example, a molecular species of interest can be a nucleic acid carrying a low frequency mutation (for example, a low frequency SNP or small deletion or insertion) that is present at low frequency in a solution relative to a corresponding wild-type nucleic acid. Alternatively, such a molecular species can be a protein having a particular configuration or binding site that is present at low frequency in a solution containing other proteins. Following segregation from other, similar molecular species the molecule of interest can be further analyzed, for example by amplification. Suitable amplification methods include PCR, reverse transcription PCR, real time PCR, and single chain ligase amplification.

The use of acridinium ester nucleic acid probes to detect a variety of nucleic acid targets has been well established. Moreover, extensively modified variants of the original acridinium ester have been shown to retain many of the singular properties of the earliest acridinium ester nucleic acid probes. The Inventors have sought to exploit a previously unappreciated property of the selective processing or reactivity of acridinium ester probes in homogenous formats, where background levels of acridinium chemiluminescence associated with mismatched targets at or near the site of the acridinium label are reduced through a base-sensitive cleavage of the acridinium label. Cleavage rates for probe-mismatched targets are much higher than the rates seen in probe-matched targets, which leave the acridinium probes on matched nucleic acid targets with the acridinium species chemically intact. In some compositions and methods of the inventive concept acridinium esters are modified to include biotin linkers positioned distal to the base-sensitive cleavage site, which can then be used to separate or enrich nucleic acid targets based on the retention of the acridinium-associated biotin linkers.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In embodiments of the inventive concept segregation is accomplished using a segregating probe. As shown in FIG. 1, such a segregating probe includes a targeting moiety component, a cleavable site component, a protective region component, and a capture hapten component. Such a segregating probe can be arranged so that the cleavable site and the protective region are interposed between the targeting moiety component and the capture hapten component. In embodiments of the inventive concept the targeting moiety component provides specific recognition and affinity-directed binding to the molecular species of interest (for example, via hybridization). It should be appreciated that such a targeting moiety component can also bind molecular species that are related to the molecular species of interest, but can do so in a distinctly different fashion (for example, by including one or more base pair mismatches). On forming a complex with the molecule of interest the segregating probe is arranged such that the protective region can prevent or slow scission of the cleavable site on initiation of a cleavage event. On forming a complex with a non-target molecular species, however, the segregating probe is arranged such that the protective region does not prevent or slow scission of the cleavable site on initiation of a cleavage event.

As shown in FIG. 1, a targeting moiety of a segregating probe is separated from a capture hapten moiety of the segregating probe by an intervening portion that includes a cleavage site. Such a cleavage site is associated with a protective region. The spatial relationship between the cleavage site and the protective region can vary between different segregating probes depending upon their purpose and/or intended target molecule of interest. In some embodiments the protective region is proximal to the cleavage site, and can be positioned between the targeting moiety and the cleavage site or, alternatively, between the cleavage site and the capture hapten moiety. In some embodiments the protective region can be a single, continuous protective group. In other embodiments the protective region can include two or more sub-regions that are not contiguous. In such distributed protective regions portions of the protective region can be distributed through different parts of the segregating construct. It should be appreciated that a protective region can be formed by the interaction between a component of a segregating probe and the target species that is separate and distinct from the interaction between the target species and the targeting moiety. In some embodiments such a protective region can be provided essentially entirely by a component of the segregating probe.

Although depicted schematically as covalent bonds, it should be appreciated that the bonds of different functional portions of a segregating probe and/or that join different functional portions of a segregating probe can be covalent, non-covalent, or a mixture of the two. For example, a segregating probe of the inventive concept can have functional portions joined by covalent bonds, charge:charge interactions, nucleotide base pair interactions, affinity interactions (e.g. antigen:antibody, carbohydrate:lectin, biotin:avidin, etc.) and/or pseudo-affinity interactions (e.g. polyhistidine:nickel).

Figure 2A:
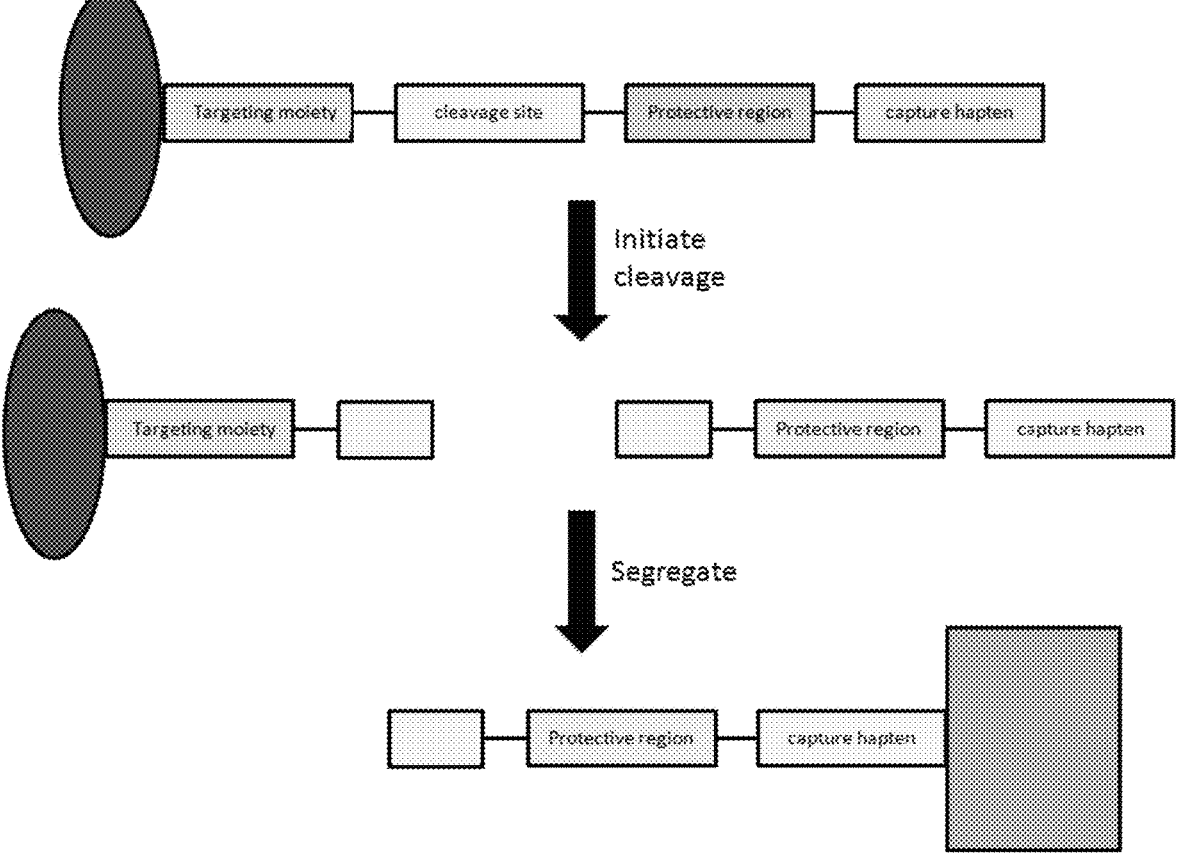
FIG. 2A.

As noted above, initiation of a cleavage event provides differentiation between the molecule of interest and non-target, but similar, molecules present in the solution. FIG. 2A schematically depicts such a reaction with a non-target molecule in solution. Although the non-target molecule may be sufficiently similar (e.g. have sufficient sequence identity) to support a degree of affinity-directed complex formation with the targeting moiety component of the segregation probe, the resulting complex does not provide protection for the cleavable site. As a result initiation of a cleavage results in scission of the segregation probe and release of the capture hapten portion from the non-target molecule. Subsequent processing steps (for example, affinity-directed isolation techniques directed to the capture hapten portion of the segregation probe), therefore, do not result in segregation of the non-target molecule with the segregating species.

Figure 2B:
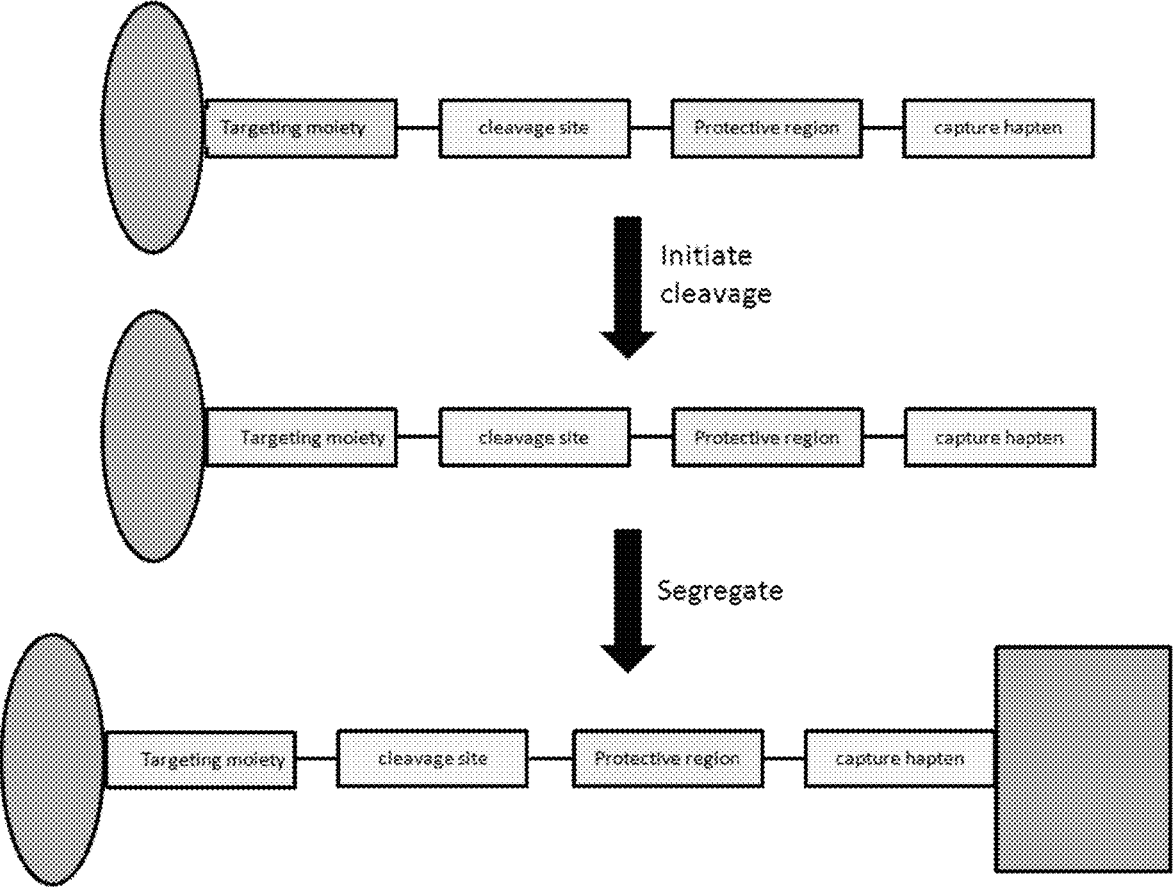
FIG. 2B.

FIG. 2B schematically depicts a reaction of a segregating probe of the inventive concept with the rare target molecule to which it is directed. Formation of the affinity-directed complex with the target molecule results in a configuration in which the protective region prevents or slows scission of the cleavable site on initiation of a cleavage event. Following such initiation, therefore, the capture hapten portion of the segregation probe is retained on the target molecule. Subsequent processing steps result in the segregation of the target molecule from other species present in the solution.

Figure 3A:
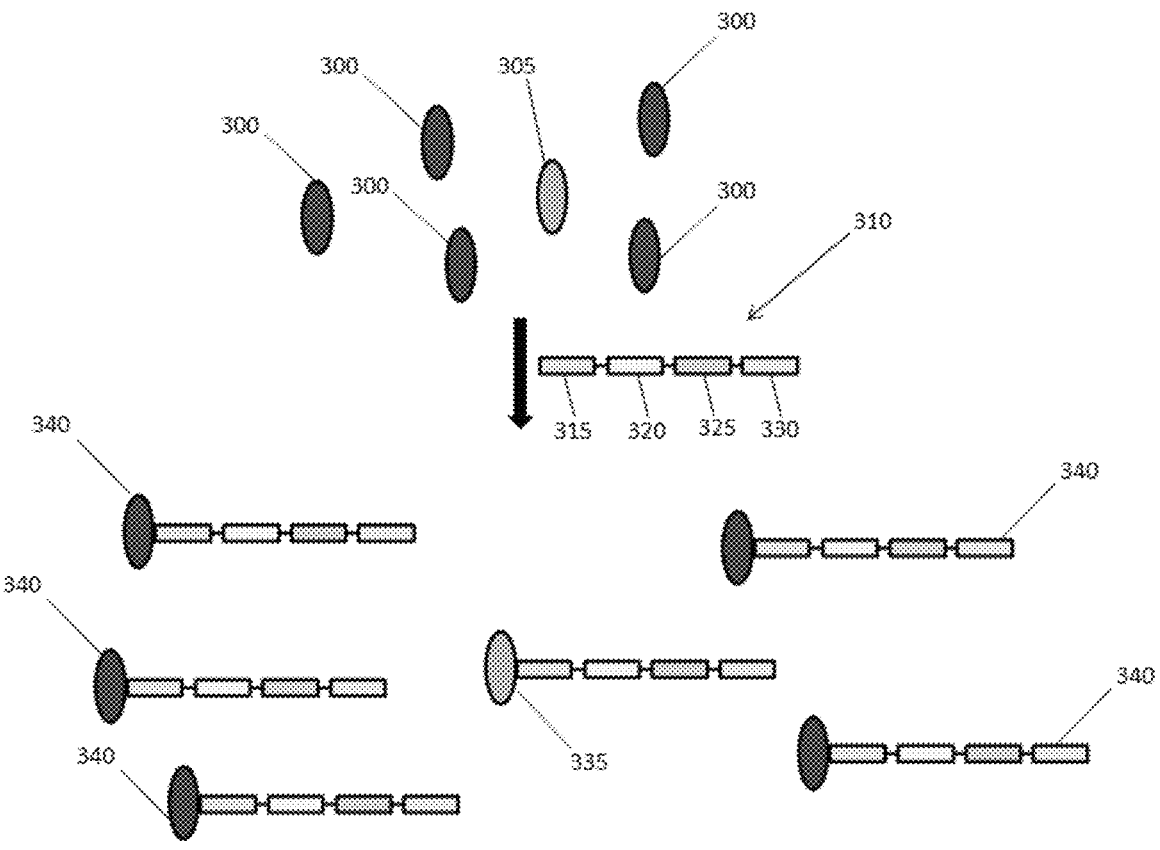
FIG. 3A.

An example of a process for utilizing such a segregation probe to isolate a rare molecular species is shown in FIGS. 3A to 3D. In FIG. 3A a solution containing numerous non-target species (300) and a rare target species (305) is combined with a segregating probe (310) of the inventive concept. The segregating probe includes a targeting moiety (315), a scissile or cleavable moiety (320), a protecting moiety (325, such as an acridinium dye or derivative thereof), and a capture tag or hapten (330). Although shown at a ratio of 5:1, it should be appreciated that a non-target species can be present at ratios ranging from 2:1 to 10,000:1 relative to the target species. As shown, the targeting moiety (315) localizes the segregating probe to the target species (305) and at least some of the non-target species (300) to form target species/segregating probe complexes (335) and non-target species/probe complexes (340).

Figure 3B:
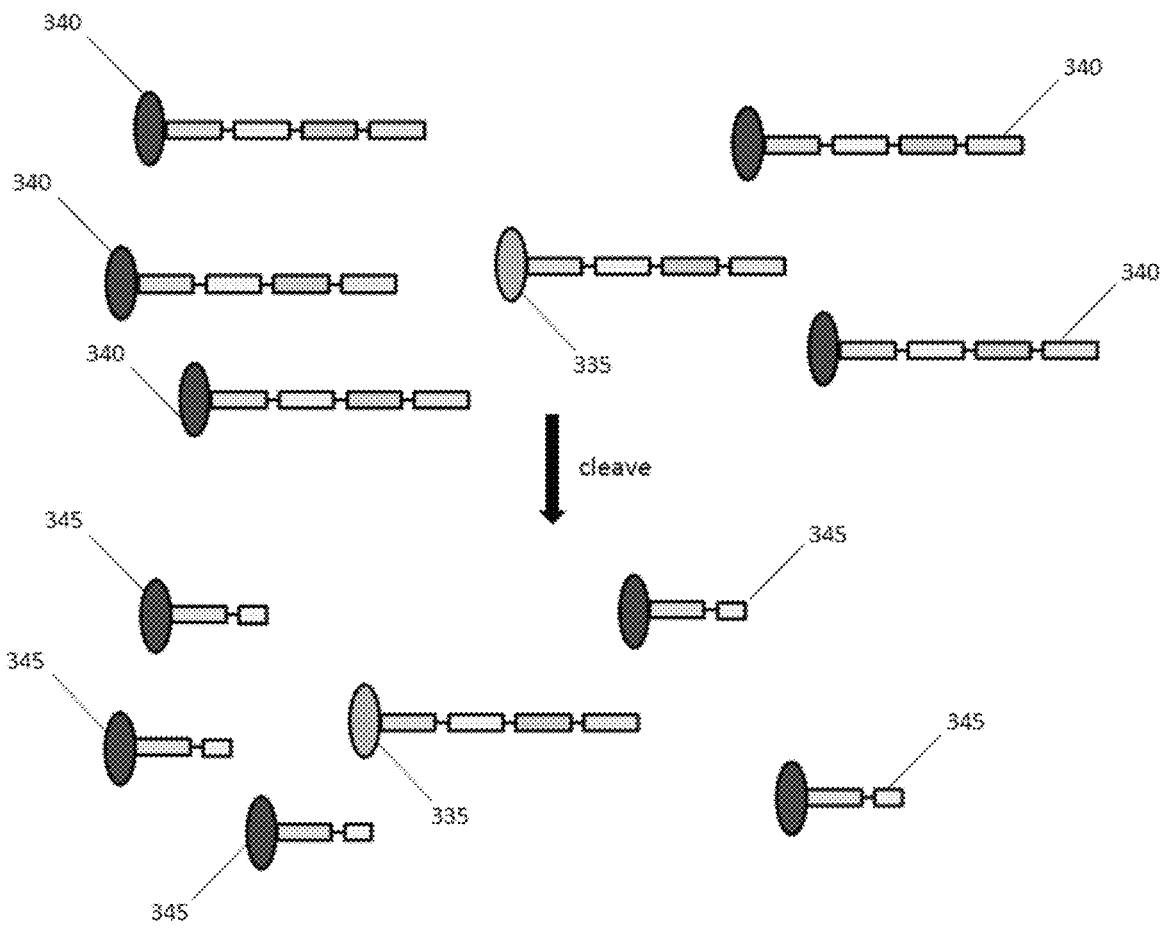
FIG. 3B.

Following binding of the segregating probe to both rare target and to non-target species, the mixture is exposed to conditions that cleave the labile cleavage site (320) of the segregating probe, as shown in FIG. 3B. In a segregating probe bound to a target species the protecting moiety (325) is arranged to prevent or slow scission of the cleavage site. For example, such a protecting moiety can interact with the bound target species in such a way as to locate the cleavage site in a protected pocket of the target species/segregating probe complex that is not readily accessible to scission-inducing species in solution. Accordingly, target species/segregating probe complexes (335) are left intact following the cleavage step. Conversely, in a segregating probe bound to a non-target species the cleavage site is accessible, and scission of the segregating probe occurs. Such scission results in the release of the capture hapten portion (330) of the segregating probe from the non-target species in a cleaved segregating probe fragment (345).

Figure 3C:
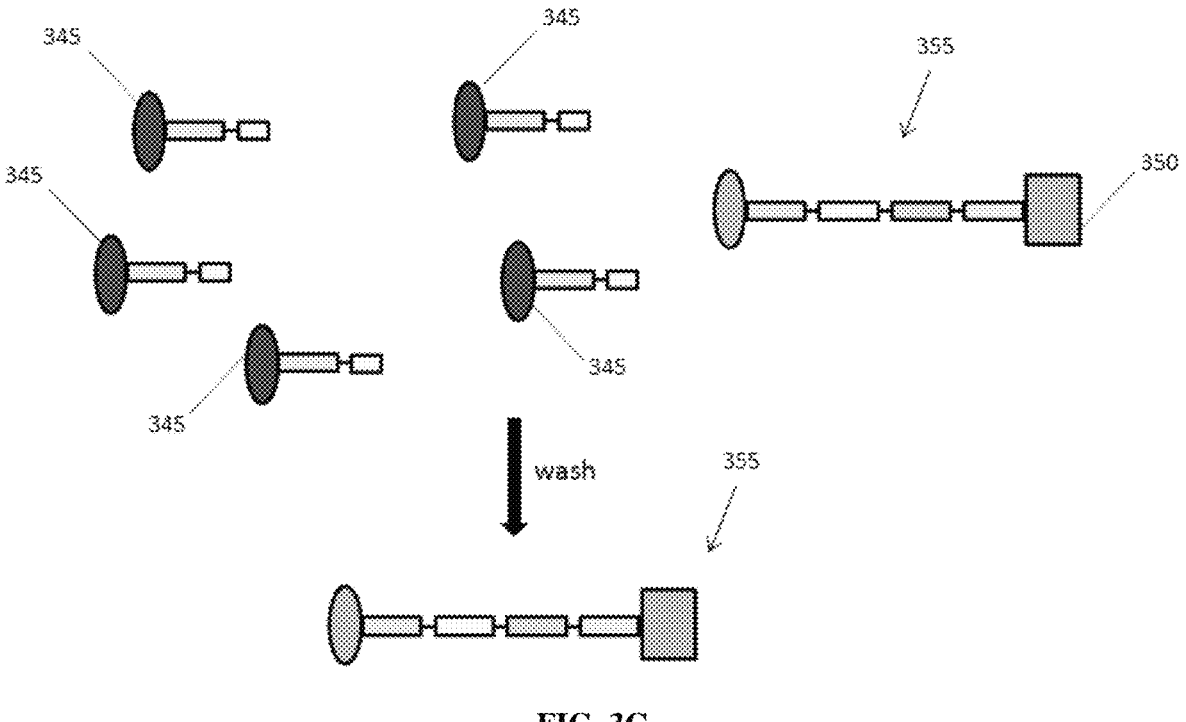
FIG. 3C.
Figure 3D:
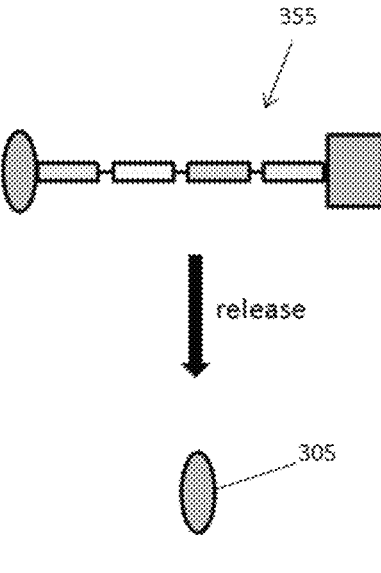
FIG. 3D.

FIG. 3C depicts a segregation step that takes place after cleavage. Exposure to an affinity partner (350) of the capture hapten portion of the segregating probe results in formation of an affinity complex (355) that associates the rare target species with the affinity partner. In a preferred embodiment such an affinity partner is provided on a solid matrix (such as a bead, particle, or microplate surface) that facilitates separation of the target species containing complexes (355) from the bulk solution. A wash step can be used to remove non-target species containing segregating probe fragments that remain in solution, leading to segregation of the rare target species (305) from the non-target species. The rare target species can be subjected to analysis at this point or can be separated from the affinity partner to yield the target species in solution. This is shown in FIG. 3D.

It should be appreciated that treatment of a large volume of sample with the segregation probe and release of the target species into a small volume effectively provides both segregation and concentration of the target species. It should be appreciated that while release of the target species is shown in FIG. 3D as being accomplished by release from the targeting moiety, in some embodiments the target species can be released from the affinity partner by disrupting the association between the capture hapten moiety of the segregating probe and the affinity partner.

It should also be appreciated that the target species can be a molecule that is associated with a larger moiety or body (for example, a protein on a cell surface). In the latter case, segregation of the target species can also provides segregation of the associated larger body. For example, a segregating probe of the inventive concept can be used to segregate a target polynucleotide carrying a SNP or small (i.e. less than or equal to 20 nucleotides) insertion or deletion that occurs at low frequency from a population containing a large excess of corresponding polynucleotides carrying the wild type sequence. Alternatively, a segregating probe directed to a rare cell surface marker can be used to segregate a cell carrying the rare surface marker from a population that includes a large excess of similar cells that do not carry the rare surface marker.

In some embodiments of the inventive concept segregation of the rare species is not carried out to completion or near completion (i.e. greater than 90% of species present being the rare target species). It should be appreciated, however, that in other embodiments of the inventive concept segregation of the rare species can be carried out for purposes of enrichment. For example, in some embodiments a rare target species can be enriched to represent 1%, 2%, 3%, 4%, 5%, 7%, 10%, 15%, 20%, 25%, 30%, 35%, 40%, and/or up to 50% of the species present. This is particularly relevant for nucleic acid applications, as amplification technologies can be implemented with useful accuracy when species are present at a few percent or more of the total population.

It should be appreciated that, while embodiments of the inventive concept illustrated above utilize positive selection (i.e. capture and segregation of the target rare species), that Inventors contemplate that compositions and methods of the inventive concept can be utilized for negative selection (i.e. capture and segregation of the non-target, common or wild-type species). For example, a segregating probe can be utilized that selectively provides a segregatable "tag" for the common or wild-type species that is not of direct interest. Segregation and subsequent removal of this common species coupled with release of the rare or target species leaves behind a population that is enriched in this target or rare species. If desired the residual sample can be subjected to repeated rounds of such negative selection in order to further enrich the residual species with the target or rare species. Such a negative selection approach can be utilized when information regarding the nature of the rare or target species is lacking.

In some embodiments of the inventive concept the targeting moiety can be a nucleic acid or nucleic acid analog sequence that is complementary or at least partially complementary to a target nucleic acid sequence. Suitable nucleic acids and/or nucleic acid analogs include DNAs, RNAs, PNAs, locked nucleic acids, and other modified nucleic acids/nucleic acid analogs, and can range in length from about 10 to about 200 nucleic acid or nucleic acid analog monomeric units in length. Nucleic acid analogs are compounds which are analogous (structurally similar) to naturally occurring RNA and DNA. Nucleic acids are chains of nucleotides, which are composed of three parts: a phosphate backbone, a pentose sugar, either ribose or deoxyribose, and one of four nucleobases. A nucleic acid analog may have any of these altered. Typically nucleic acid analogs confer, among other things, different base pairing and base stacking properties. Examples include universal bases, which can pair with all four canonical bases, and phosphate-sugar backbone analogs such as PNA.

Artificial nucleic acids include peptide nucleic acid (PNA), Morpholino and locked nucleic acid (LNA), as well as glycol nucleic acid (GNA) and threose nucleic acid (TNA). Each of these is distinguished from naturally occurring DNA or RNA by changes to the backbone of the molecule. Such a nucleic acid or analog based targeting moiety can be linear or branched, and can include circular and/or hairpin structures.

In other embodiments of the inventive concept the targeting moiety can be a peptide or peptide analog that has an affinity for a target site of a protein or other macromolecule. Such a target site can include a minor structural modification that is insufficient for differentiation from a native configuration by conventional (e.g. immunochemical) means, but that provides sufficient differentiation for deprotection in compositions and methods of the inventive concept. Such peptides can include immunoglobulins and/or immunoglobulin fragments (e.g. $F(ab)_2$, $F(ab)'$, etc.), single chain antibodies, etc. Such peptides can also include peptides corresponding to enzyme active or recognition sites, cell surface receptor binding sites, and lectin binding sites. In some embodiments of the inventive concept the peptide analog can be a dendrimer.

In still other embodiments of the inventive concept the targeting moiety can be a small molecule (i.e. a molecule with a molecular weight of less than 1,000 D). Examples of suitable small molecules include saccharides (e.g. mono, di, tri, and higher order saccharides), lipids, pharmaceutical compounds, and dyes.

The capture haptens of the segregating probe provides a means to separate a species that has complexed with the targeting moiety from the surrounding milieu. In a preferred embodiment the capture moiety has an affinity for a capture species that is coupled to or otherwise colocalized with the affinity partner. Such an affinity partner can provide phase separation that is readily separable from the solution containing the target and non-target species. For example, a suitable affinity partner can be a particle, microparticle, bead, fiber, filament, mesh, or other solid surface (for example, the well of a microwell plate or interior of a pipette tip) that includes a capture species. In some embodiments of the inventive concept the affinity partner can be magnetically responsive. Suitable capture haptens include small molecules such as biotin and/or biotin analogs (such as iminobiotin), haptenic groups (such as digoxigenin or dinitrophenyl), saccharides, peptides (for example, polyhistidine), and nucleic acids. Corresponding capture species include avidin, modified avidins, streptavidin, hapten-specific antibodies or antibody fragments, lectins, metals (for example, nickel), and complementary nucleic acids. In some embodiments the capture hapten can be selected to readily release from the affinity partner under conditions that retain the activity and/or structure of the rare species being captured. For example the capture hapten can be iminobiotin (which is readily released from avidin and streptavidin by competition with biotin), a saccharide that is readily displaced from capture lectin by competition with free saccharide, or a polynucleotide that is readily released from a complementary polynucleotide by a change in temperature and/or salt concentration.

Cleavable groups of the segregating probe can be selected to undergo scission under conditions that retain the structure and/or activity of the desired rare species. Within the context of this application, such cleavable or scissile groups are understood to include scissile bonds (either covalent or non-covalent) that can be broken while remaining bonds (either covalent or non-covalent) of the segregating probe structure remain intact. Examples of suitable cleavable groups include organic cleavable groups (e.g. carboxylate esters, sulfo-esters, etc.), peptides (e.g. peptides that act as protease substrates), and nucleic acid sequences (e.g. sequences that act as restriction enzyme substrates). Such cleavable groups are selected in concert with the protecting group so that scission is reduced or prevented on complex formation with the rare target species.

For example, an organic cleavable group can be selected to be a chemical linkage that includes an ester bond, which can undergo scission under mildly alkaline conditions when exposed outside of the protecting group. Other organic cleavable groups can undergo scission under acidic conditions, in the presence of oxidizing agents, in the presence of reducing agents, and/or when subjected to electromagnetic radiation when they are exposed outside of the protecting group. In a preferred embodiment of the inventive concept the cleavable group is an ester, and can be protected within the minor groove of a DNA duplex in the presence of an acridinium dye.

As noted above, the protecting group is selected in concert with the cleavable group and in consideration of the nature of the target species. In some embodiments of the inventive concept the protecting group interacts with the structure of the target species such that it is interposed between the cleavable group and the external milieu when the segregating probe complexes with the rare target species, but is not so interposed when the segregating probe complexes with the similar non-target species. For example, an acridinium dye can position within a minor groove of a DNA duplex and serve as a protecting group for an organic cleavable group that includes a labile ester bond when the segregating probe is directed to a nucleic acid that includes a target SNP, whereas the single base mismatch produced by complex formation between the segregating probe and a similar native nucleic acid sequence (i.e. one that does not include the target SNP) results in a disruption of the minor groove and displacement of the acridinium dye. Such displacement can expose the labile ester bond and result in scission of the segregating probe. It should be appreciated that the protecting group can incorporate elements of both the segregating probe and the target species, for example forming a protecting region through interaction between a minor groove of a DNA duplex and a complexing dye. In other embodiments the protecting group can be essentially completely incorporated into the segregating probe, for example through incorporation of quenching groups that act to absorb electromagnetic radiation that would otherwise disrupt a photolabile cleavable group.

In some embodiments of the inventive concept the target species is a nucleic acid that includes a single nucleotide polymorphism (SNP) characteristic of a tumor cell. Tumor cells that include the characteristic SNP may be present at low frequency in a tissue or blood sample that contains numerous cells carrying the wild genotype (i.e. one lacking the target SNP). Similarly, nucleic acids (e.g. DNA, RNA) carrying such SNPs may be present in free form in circulation, along with numerous copies of wild type nucleic acid that does not carry the target SNP. In some embodiments of the inventive concept the protecting group of such segregating probes can include an organic moiety that complexes with specific structures that form part of the target species: segregating probe complex (for example, a minor groove of a DNA; DNA duplex). Exemplary embodiments of such organic moieties and segregating probes based on them follow.

Figure 4:
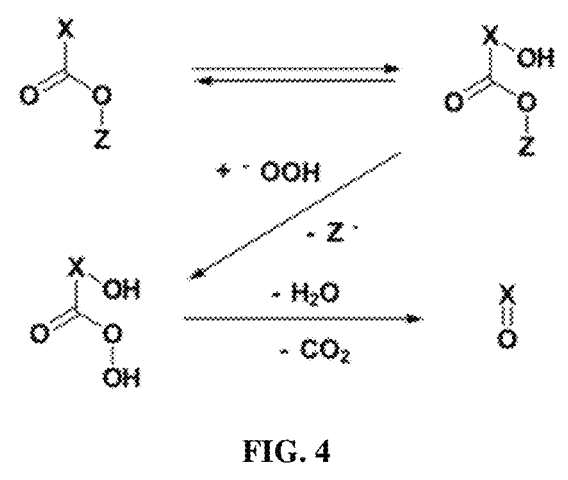

Some embodiments of the inventive concept are directed to base-sensitive linkers and methods of use thereof, such as, for example, in enhancement of rare nucleic acids, that contain single nucleotide polymorphism, using segregating probes, in molecular diagnostics and/or in-vitro diagnostics. An exemplary embodiment is shown in FIG. 4. The reaction begins with the attack by mild alkaline sodium borate anions on a target segregating probe compound. Under alkaline conditions an alcohol intermediate is formed, followed by rapid conversion to an excited X-ketone compound. This reaction cleaves unbound target segregating probes to leave only bound duplexes of target segregating probe and rare nucleic acids that are protected by hybridized target segregating probes.

The inventive concept encompasses the chemical compounds and their reaction mechanism processes, that are used for target segregation, isolation, separation, and/or purification of rare nucleic acids from a mixture having a minor quantity of rare nucleic acids and an excess of wild-type genes (which can be obtained from a biological system). After sample preparation steps, the isolated rare nucleic acids can optionally be amplified, and/or analyzed by conventional techniques.

Some embodiments of the inventive concept employ compounds that localize in the minor groove of the double stranded nucleic acid helix, such as acridinium dyes or dye derivatives as scissile or cleavable portion of a segregating probe. In such embodiments a portion of the minor groove can exclude the aqueous solvent and act as a protecting group when a perfect base match is provided. Disruption of the minor groove by a base mismatch, however, can expose the acridinium dye exposed when a mismatch occurs. Suitably labile acridinium dye esters (AEs) are available.

In some embodiments of the inventive concept, a segregating probe can include a scissile portion that includes an acridinium dye ester. Pringle, M. J., Journal of Clinical Ligand Assay vol. 22, pp. 105-122 (1999) has found that such compounds undergo ester cleavage on reaction with alkaline peroxide. In such embodiments the dye can include an ester linkage positioned between the organic ring structures of the dye.

In another suitable class of acridinium dye compounds the phenolic ester linkage is replaced by a sulfonamide moiety, as described by Kinkel et al., Journal of Bioluminescence and Chemiluminescence vol. 4, pp. 136-139 (1989) and Mattingly, Journal of Bioluminescence and Chemiluminescence vol. 6, pp. 107-114 (1991) and U.S. Pat. No. 5,468, 646. Such acridinium dye sulfonamides are susceptible to cleavage by alkaline peroxide. Whereas acridium dye esters the phenol is a 'leaving group', in such acridinium dye sulfonamides the sulfonamide is the 'leaving group'. In some embodiments of the inventive concept a specific mild hydrolysis buffer can be used to cleave an acridinium dye sulfonamide.

Some methods and compositions of the inventive concept are directed to a "three-membered-ring" compound, such as a dye or any organic group that creates an instability in the linkage (e.g. a carboxylic ester or sulfonamide ester), which in turn links the compound to a phenol group (or any suitable group) that acts as a leaving group.

Figure 5:
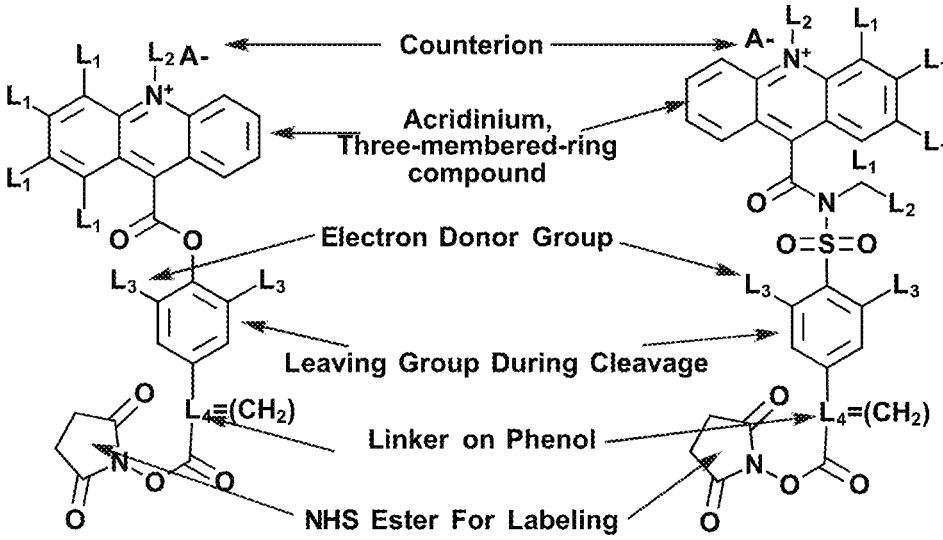
FIG. 5.

In some embodiments of the inventive concept such compositions can be used to selectively enrich a test mixture's content of a rare nucleic acid prior to the detection and/or identification of the rare nucleic acids (e.g. by using conventional amplification, hybridization, and/or sequencing technology). Exemplary compounds useful for this purpose are shown in FIG. 4. The component X (such as a dye compound) and the component Z (such as phenol group) on the segregating probe maintain the balance in electron contributions to the Y-linkage (e.g. a carboxylic ester linkage or sulfonamide ester linkage) interposed between the components X and Z. Counterintuitively, these linkages must be unstable, for example being cleavable by mild hydrolysis reaction as shown in FIG. 4. The dye compound (for example, an acridinium dye) can include a linker group L1, covalently attached to the position C-1, C-2, C-3, and/or C-4 on a benzene ring or similar organic structure, and/or linker group L2, covalently attached to a quaternary center N-10 atom of a dye nucleus. L1 can be linked by carbamate (—NH—CO—), ether (—O—), and/or thio-ether (—S—) groups with linkers that contribute to the solubility of the molecule, and L2 can be linked by a carboxylate ester (—CO$_2$—), or sulfonamide ester (—SO$_2$—NH—) ester linker group between an acridinium nucleus and a binding group such as biotin, as shown in FIG. 5. Structures of two dye esters are used as target captures, where dye accesses cleavage on the carboxylate ester, and sulfonamide ester, assisted by a phenyl leaving group. L1, L2, and L3 can be electron donors (such as methyl, fluoride, bromide, and/or chloride) and L4 can include one, two, or more carbons. L1, L2, L3, and L4 can include a linker, which links to a capture moiety (such as biotin or a biotin-like compound) used for binding to a protein or other capturing species on magnetic beads.

Figure 6:
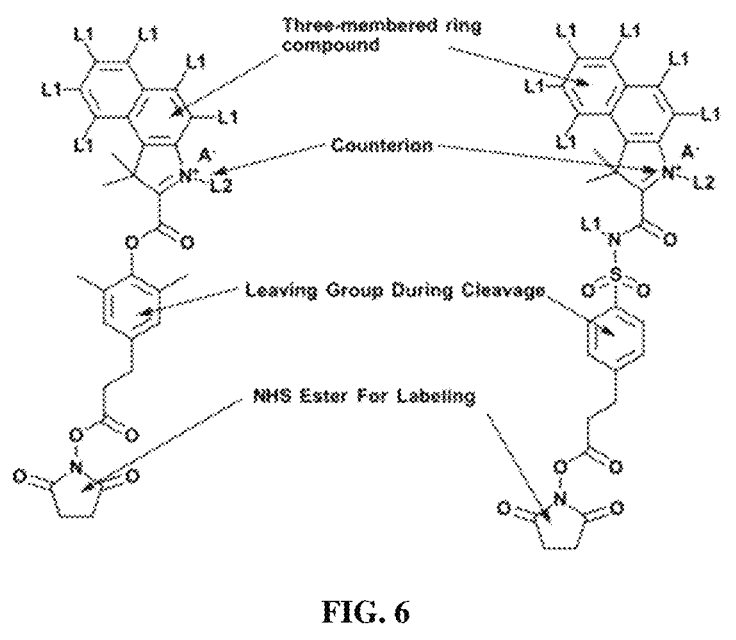
Figure 7:
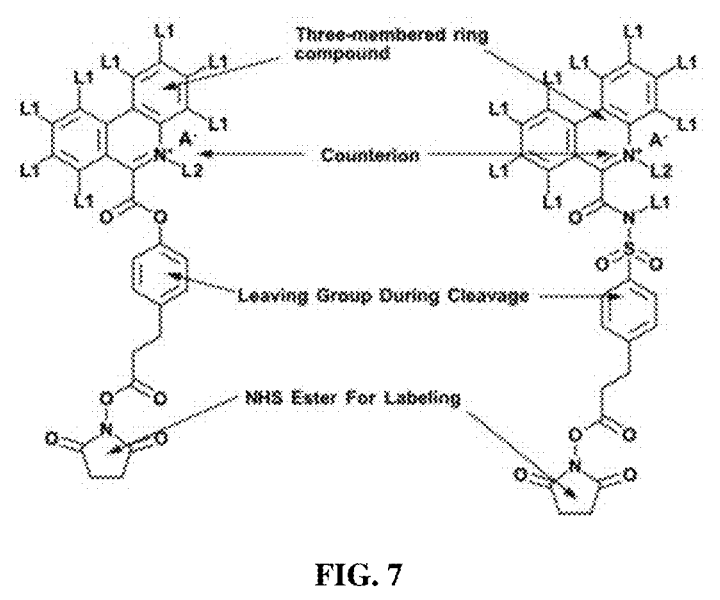

Suitable dye compounds can be light emitting compounds such as those shown in FIG. 5, although light emission is not necessary for the segregating function. Light emitting compounds that have the cleavage reaction similar to the dyes noted above are shown in FIG. 6, where L1 is H or and aliphatic amine, and L2 is a sulfonylpropionate-linker. FIG. 7 depicts related compounds that include a three-membered ring with a counterionic salt to contribute the instability to the ester linkage, and with phenyl leaving group, which contains an amine-reactive NHS-ester.

Figure 8:
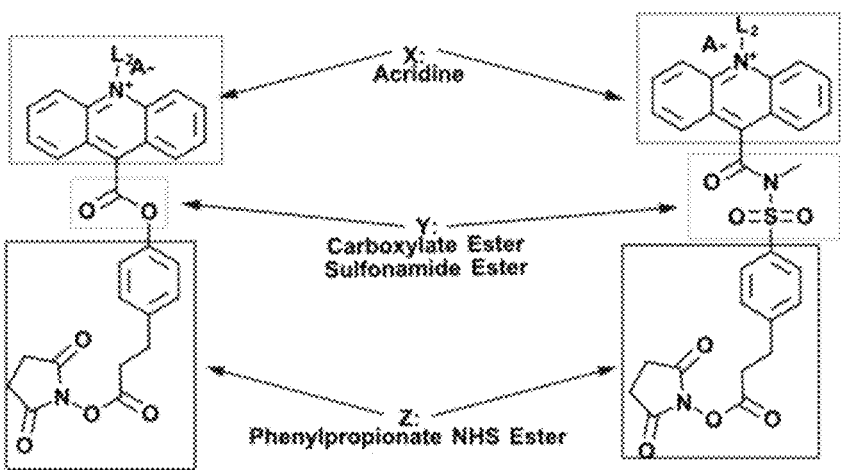
FIG. 8: Generic structures of exemplary segregating probe intermediates. X and Z are chemical groups of a segregating probe intermediate, that are linked by a linkage: a carboxylate ester, or a carbonyl sulfonamide ester. L2 is linked to propyl sulfonyl group, which contains linker and a binding moiety, such as biotin. The Z moiety provides a reactive group suitable for coupling to a targeting moiety.
Figure 9:
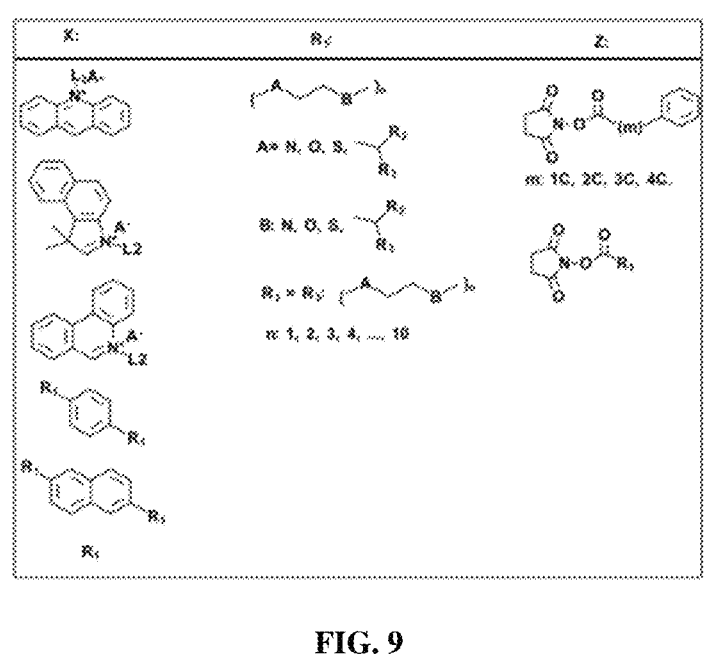

General Chemical Groups Useful as a Segregating Probe or Segregating Probe Intermediate Generic structures of exemplary segregating probe intermediates are described as X, Y, and Z, as shown in FIG. 8, where R1, R2, R3 are linkers, n is the number of building blocks of the linkers, and m is number of carbons that are included in the structures. X and Z are chemical groups of a segregating probe intermediate, which are linked by a linkage such as a carboxylate ester, or a carbonyl sulfonamide ester. L2 is linked to propyl sulfonyl group, which includes a linker and a binding moiety, such as biotin. The Z moiety provides a reactive group suitable for coupling of such an intermediate compound to a suitable targeting moiety. Exemplary X, Y, and Z chemical groups of segregating probe intermediates are shown in FIG. 9.

Cleavage Reaction Mechanisms

Figure 10:
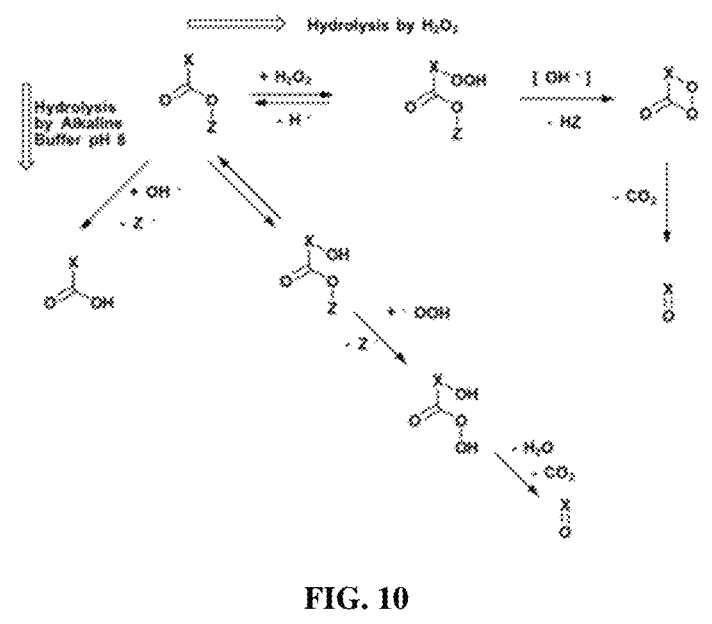

Inventors contemplate that cleavage of segregating probes incorporating one or more of the X compounds, such as a dye ester, can be accomplished by a variety of means. Short-lived intermediates are considered part of the processes leading to decarboxylation, and lead to the cleavage of ester linkage. The processes proposed for an X ester, resulting in cleavage of the ester, can proceed by different pathways. For example, a fast reaction which uses alkaline hydrogen peroxide buffer can provide complete cleavage. Alternatively, a mild reaction which uses mild alkaline sodium borate buffer can provide selective cleavage at the ester linkage. Such hydrolysis reactions are schematically shown in FIG. 10. The ester can also be cleaved using an alkaline buffer. The mechanism is shown for two hydrolysis pathways. The fast, nonselective reaction using hydrogen peroxide cleaves all esters, whereas the mild reaction using sodium borate buffer at about pH 8, cleaves esters selectively.

In a first hydrolysis pathway using H$_2$O$_2$, the carbonyl group, which had been part of an amide or ester bond, becomes part of a dioxetanone moiety. Spontaneous decomposition of the dioxetanone moiety is accompanied the production of a heterocyclic ketone and CO$_2$ (in case of a segregating probe incorporating a carbonyl group), or in more general chemical terms a heterocumulene.

Alternatively, in a second hydrolysis pathway using a mild alkaline buffer (such as borate) at about pH 8, the reaction begins with an attack by mild alkaline sodium borate anions on a segregating probe compound. Under alkaline conditions an alcohol intermediate is formed, followed by rapid conversion to an excited X-ketone compound. This reaction selectively cleaves only unbound segregating probes to leave only bound duplexes of segregating probe and rare nucleic acids that are protected by hybridization. Methods of the inventive concept can use such a selective hydrolysis to cleave ester linkages of unbound target.

As shown in FIG. 10, the cleavage reaction is dependent on the properties of the leaving group Z. An essential feature of the X compound used in target capture applications is that the ester function has been substituted to provide a suitable leaving group Z. Suitable leaving groups are designed to provide (as far as possible) two essential requirements: stability and high quantum yield. On the one hand the leaving group of an X ester must be as active as possible, i.e., leaving quite readily under measurement conditions, to allow for a sensitive capture and high yield. This high activity on the other hand, however, is at the expense of instability towards hydrolysis. Such instabilities are even more critical if such target captures are used for conjugation to biomolecules. The goal to achieve a high yield and in addition a high stability of the labeled reagent a balance between yield and stability. To at least partially reduce the problems encountered, novel and different leaving groups have been considered and designed.

One embodiment of a segregating probe molecule for capturing the nucleic acid includes substituents and linkages with specific electrons balances an include:

1) A capture moiety or hapten such as biotin or iminobiotin, which provides strong binding to a specific capture moiety (such as an antibody, antibody derivative or fragment, avidin, and/or streptavidin). Potential capture moieties include biotin, iminobiotin, digoxigenin, polyhistidine, antigenic haptens, nucleotide sequences, etc.

2) An electron donor group, such as a three-membered ring of a quaternary organic compound, that influences the cleavage of an ester linkage or other cleavable linkage.

3) A cleavable linkage, such as a carboxylate ester (R—CO—O—R) or sulfonamide ester (R—CO—N—SO$_2$—R), that is labile enough to be cleaved when exposed to mild alkaline sodium borate buffer, but stable enough so that segregating probe complex remains intact when the cleavable linkage is protected (e.g. by hybridization).

4) Optionally, an intermediate in the synthesis of a segregating probe can include a sensitive leaving group such as propionyl phenolic group, which can contain a reactive group (such as an NHS-ester, aldehyde, maleimide, epoxide, etc.) for labeling targeting moiety, such as an antibody/antibody fragment or a nucleic acid probe sequence that is complementary to a rare sequence.

Figure 11:
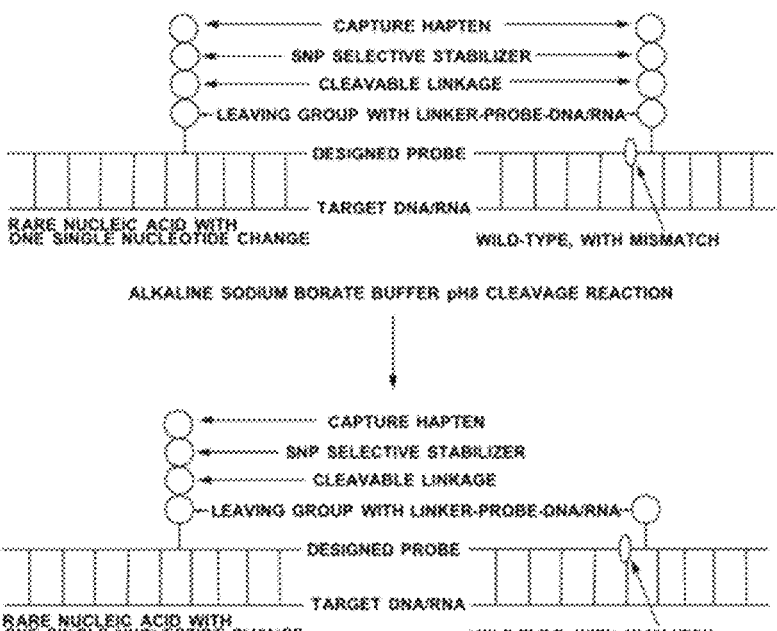
FIG. 11.

In a preferred embodiment, segregating probes and methods of the inventive concept are utilized to isolate a rare polynucleotide from a milieu containing a preponderance of related polynucleotides differing by a single base, as shown in FIG. 11. A segregating probe intermediate including the portions described above can be synthesized and coupled to a nucleic acid complementary to the rare polynucleotide and containing an amino-linker that is reactive with a reactive group of the segregating probe intermediate. The segregating probe, which can be provided in excess in order to improve reaction kinetics, is then hybridized to the rare polynucleotide in a hybridization buffer (for example, a buffer have a pH from 6 to 10). Unbound segregating probe and segregating probe hybridized to the mismatched polynucleotides (e.g. wild-type), in which the cleavable portion of the probe is not protected, are subsequently cleaved at the scissile bond (e.g. an ester or sulfonamide linkage). The matched polynucleotide/segregating probe hybrid, which can be protected by minor groove binding, remains intact. The capture compound, (e.g. biotin) is captured using magnetic beads (e.g. streptavidin coated magnetic beads) in an isolation step. The unbound polynucleotides and excess cleaved segregating probe can be washed (e.g. by extraction with a magnet followed by buffer exchange) to remove or reduce the amount of non-target (e.g. wild type) polynucleotide. An example of such a process is depicted schematically in FIG. 11. The left side of the figure shows hybridization of the segregating probe with a target polynucleotide. The hybridized segregating probe includes four functional blocks: L1, or L2, X, Y, and Z, which remains intact following the cleavage reaction. The right side of FIG. 11 depicts the same segregating probe hybridized with the wild-type polynucleotide, which loses three functional blocks (L1 or L2, X, Y) on cleavage. The binding moiety (e.g. biotin) is lost, and only the leaving group and linker remains in such a duplex.

Figure 12:
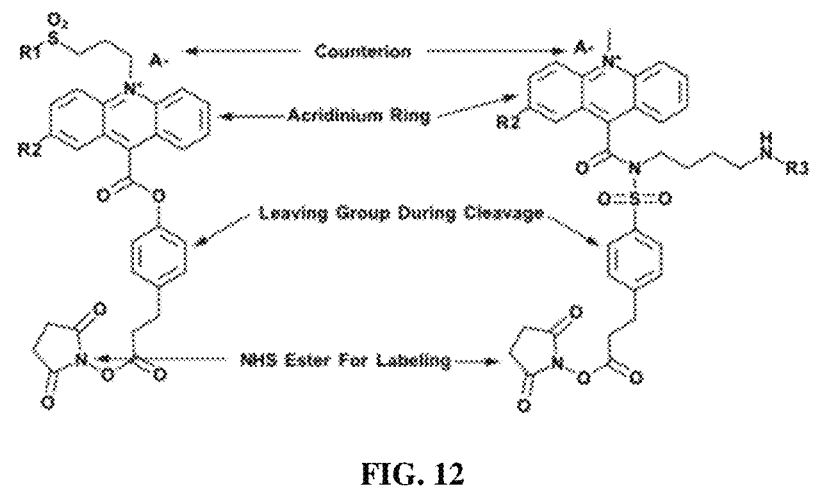

In some embodiments of the inventive concept the binding moiety (e.g. biotin) can be attached to chemical group that contributes to protection of the cleavable or scissile linkage (such as acridine) at position Carbon C2, or at quaternary Nitrogen N-10, in L1, and L2, that are in turn linked to a reactive group, such as an NHS-ester. A scissile bond can be understood within the context of this application to be a bond (either covalent or non-covalent) within a segregating probe that can be selectively broken while leaving remaining bonds (either covalent or non-covalent) within the segregating probe (or fragments thereof generated by such cleavage) intact. Such a binding moiety can be attached to a nitrogen of sulfonamide linkage sulfonamide NHS-Ester at L2. Examples of possible structures of such molecules are depicted in FIG. 12, which shows the chemical structures of two exemplary segregating probe intermediates (biotin dye NHS-ester, and biotin dye sulfonamide NHS-ester). Such compounds can include 1) a counterion A-, 2) a three-membered ring acridinium, 3) a labile linkage (e.g. ester or sulfonamide), 4) a leaving group lost during cleavage, and 5) a reactive group (such as an NHS-ester) for coupling to a targeting moiety.

Structures of Exemplary Segregating Probes, and the Hybridization Protection Function General structures of segregating probes and segregating probe intermediates can have the following characteristics:

A) The structures of segregating probe intermediates are designed using three chemical building groups: 1) binding or capture moiety, such as linker-biotin, 2) a cleavage access moiety, such as a dye, and 3) a leaving group, such as phenyl-p-propionate-NHS ester. In a segregating probe such a leaving group will have reacted with a targeting moiety, such as a polynucleotide complementary to a rare target sequence.

B) A binding group, such as biotin can be coupled at a single position to the cleavage-access group, such as three-member ring of the acridine (green box) at position 1,2,3,4, or 10, using carbamate (—CO—NH—), ether (—O—), or thio-ether (—S—) linkages. The substitution using carbamoylamide (—CO—NH—) linkage (see 1301 of FIG. 13), or attached through quaternary nitrogen at position N-10 (see 1302 of FIG. 13).

C) A plurality of binding groups, such as biotin can be substituted at multiple positions, such as positions 1, 2, 3, 4, 5, 6, 7, 8, using the same above linkages described in B), to make a multi-biotinyl-dye.

D) A biotinyl-dye group, can be linked to a p-phenyl-propionate NHS ester group by a labile linkage (such as an ester), which can be cleaved by treatment with a mild alkaline sodium borate buffer.

E) Methyl, sulfonyl-alkyl, and/or halogen atoms (such as fluoride, chloride, or bromide) can be substituted to a p-phenyl-propionate NHS ester group to create mono-substitution at ortho or meta-positions, or multi-substitutions at all available positions on the benzene ring.

Figure 13:
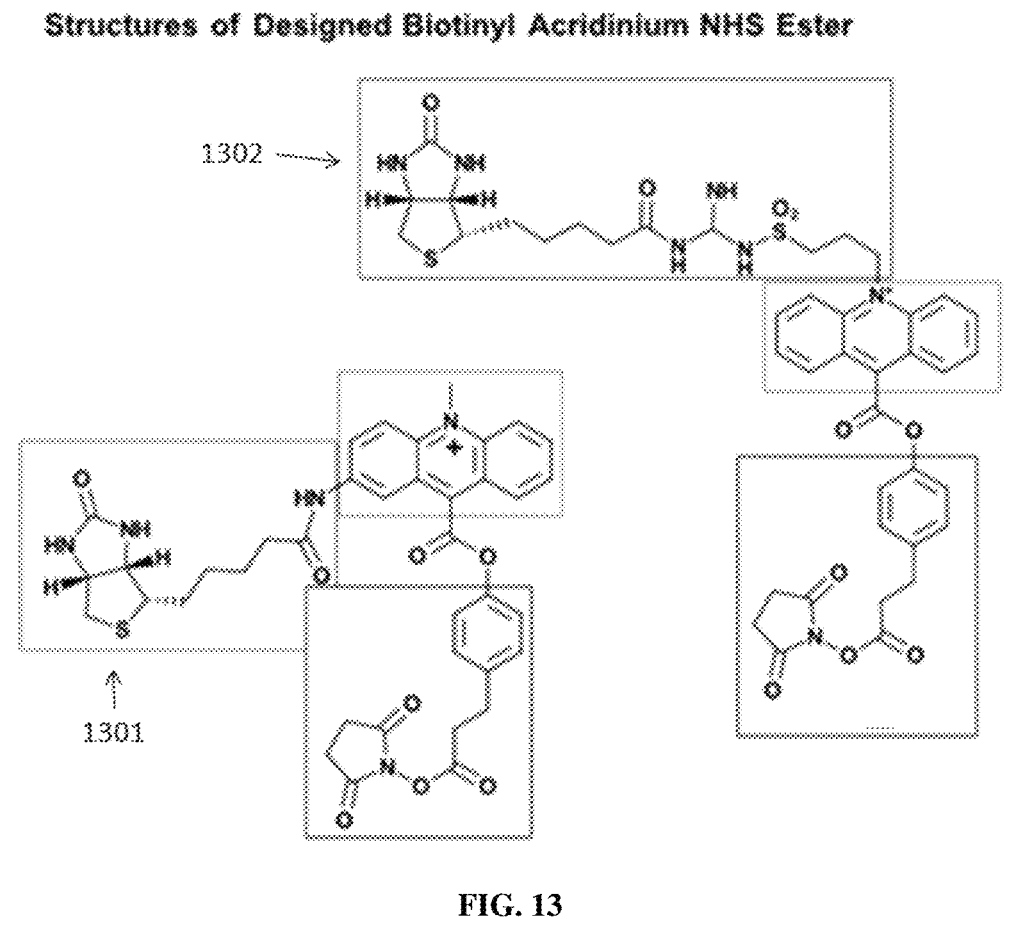

FIG. 13 shows the structures of two segregating probe intermediates based on biotinyl dye NHS esters and including three chemical building blocks. Each has a specific function in a sample preparation process based segregating probes produced using such segregating probe intermediates. The ester linkage of such molecules can be stable under the cleavage by mild sodium borate buffer pH 8, when hybridized to a target rare polynucleotide.

An exemplary method for sample preparation and detection of polynucleotides can include the following steps:

A) A binding group, such as biotin is linked to a portion of a segregating probe intermediate, such as a dye-NHS ester of a probe intermediate, through three-member ring at position C-2, by carbamate, ether, thio-ether linkage, or at quaternary nitrogen position N-10. The binding compound, such as biotinyl dye-NHS ester, can, for example, couple to a free amino group on the linker of a DNA sequence complementary to a specific target rare polynucleotide.

B) Probe Hybridization: The biotin-dye-ester-linker probe containing an appropriately complementary nucleic acid sequence for hybridizing to the target polynucleotide is added to specimen (such as blood, serum, plasma, macerated tissue, and other body fluids) thought to contain the rare polynucleotide in a hybridization buffer and incubated (for example, for 10 minutes at 60° C.).

C) Unbound/Mismatched Probe Removal: A mild alkaline borate buffer (for example, lithium borate at pH 8) is added to the mixture and mixed. After a suitable incubation (e.g. at 60° C. for 20 minutes) the biotin-dye-linker-probes that are unbound and/or formed mismatched duplexes are selectively cleaved by the borate buffer. Only the matched biotin-dye-linker-probes that bound perfectly to rare polynucleotides remain intact in the buffer solution.

D) Sample Preparation Completion: Streptavidin-modified magnetic beads are added to the solution to form streptavidin-biotin-linker-probe bound target nucleic acids. The resulting magnetic beads after bound are then washed using an appropriate buffer solutions to remove unbound materials, and can be dried. Sample preparation can performed using an automated system.

E) The purified rare target polynucleotides can be analyzed, for example through conventional amplification, hybridization, and/or sequencing techniques. In some embodiments this step can be performed directly on the magnetic beads carrying the target nucleic acid. In other embodiments the target nucleic acid can be released from the magnetic bead (for example by elevated temperature, reduced salt concentration, and or protease treatment) prior to analysis.

It should be appreciated that portions of a segregating probe, for example linker regions that join functional portions (e.g. targeting moiety, capture moiety, protecting region, and/or cleavable/scissile site) can include spacer portions. Such spacer portions do not participate directly in the above described functions of the segregating probe, but rather provide spacing, positioning, and/or geometry that permits or enhances their function. As such, a spacer portion can be flexible or rigid. Spacer portions can be of any suitable length, for example from 3 to 4 carbons to 48 carbons (or more) in length. Spacer portions can be provided during synthesis (for example, in synthetic routes outlined below) by choice of suitable starting compounds and/or by repetition of additive synthetic steps during synthesis of the spacer portion (for example, successive additions of amino-hexanoic acid).

Examples

Exemplary Synthesis A

Synthesis of an 2-Biotinyl Dye NHS Ester

Figure 14:
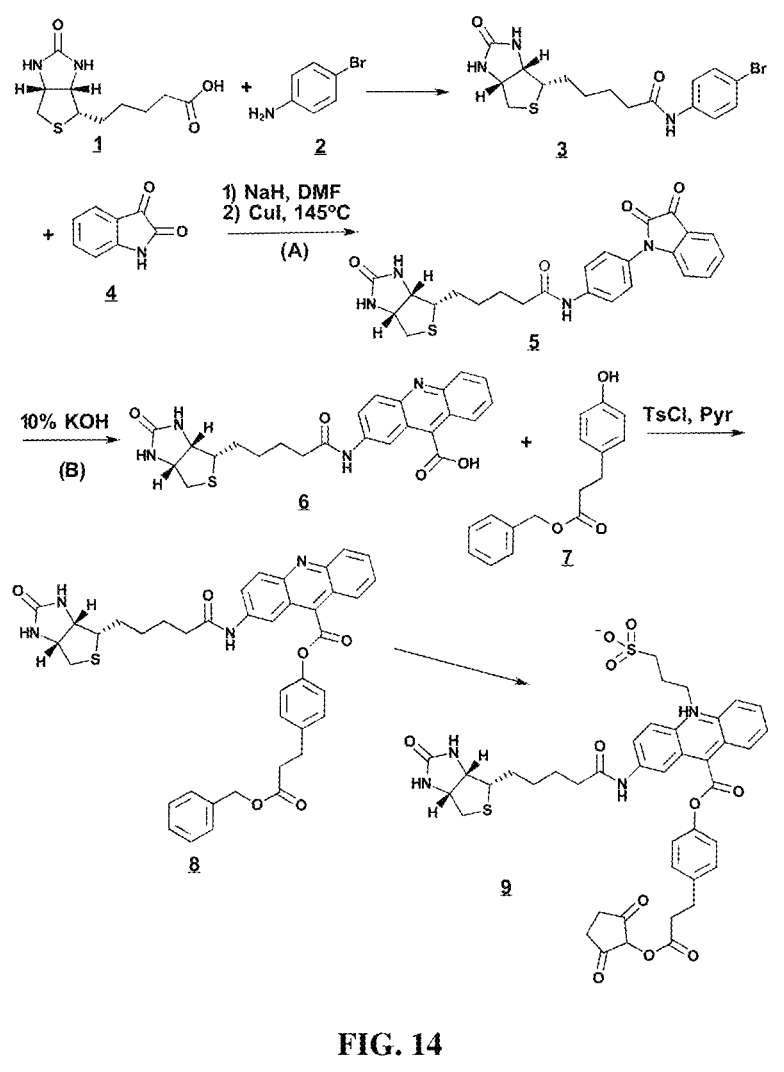
Figure 15:
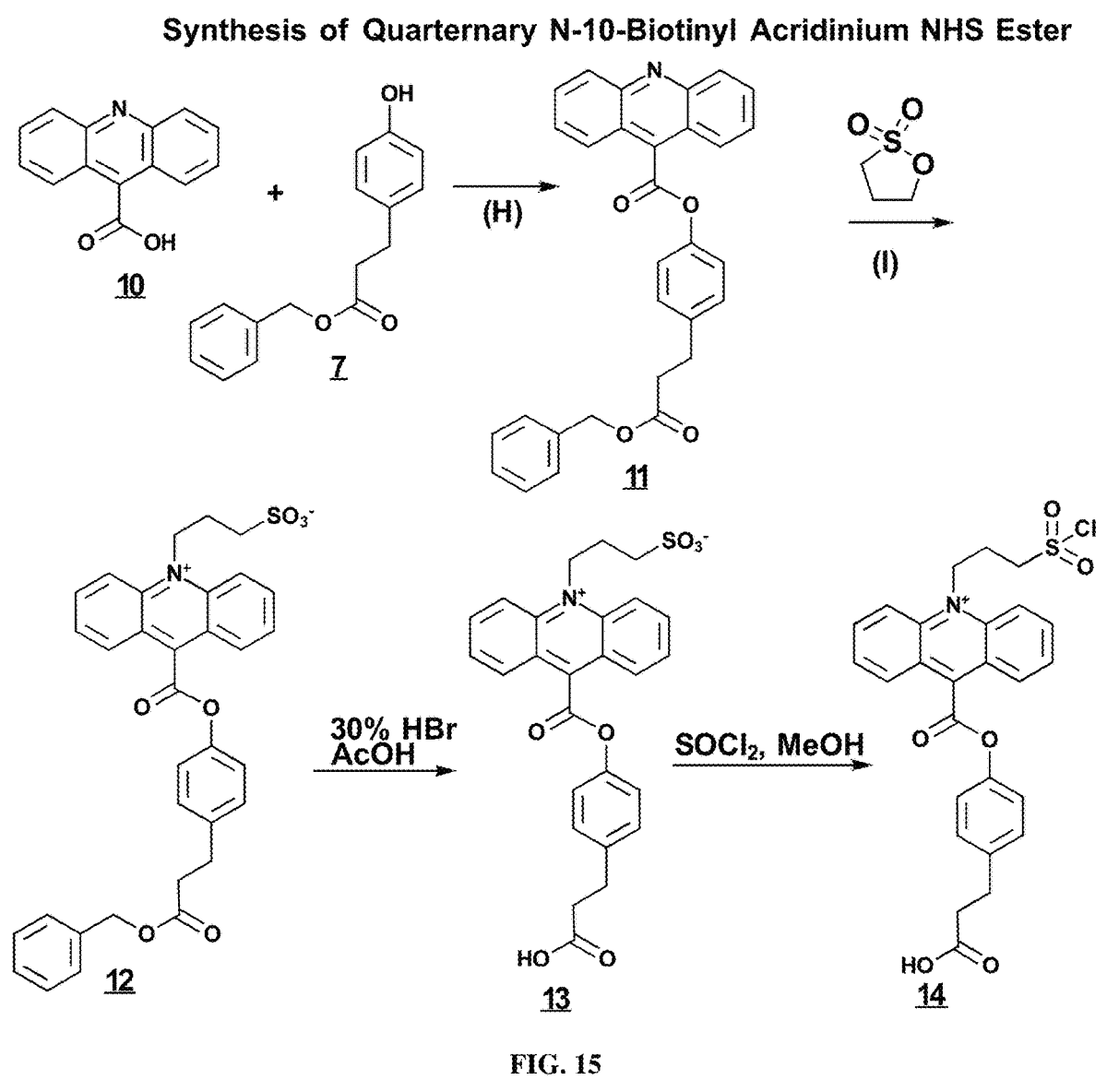
Figure 16:
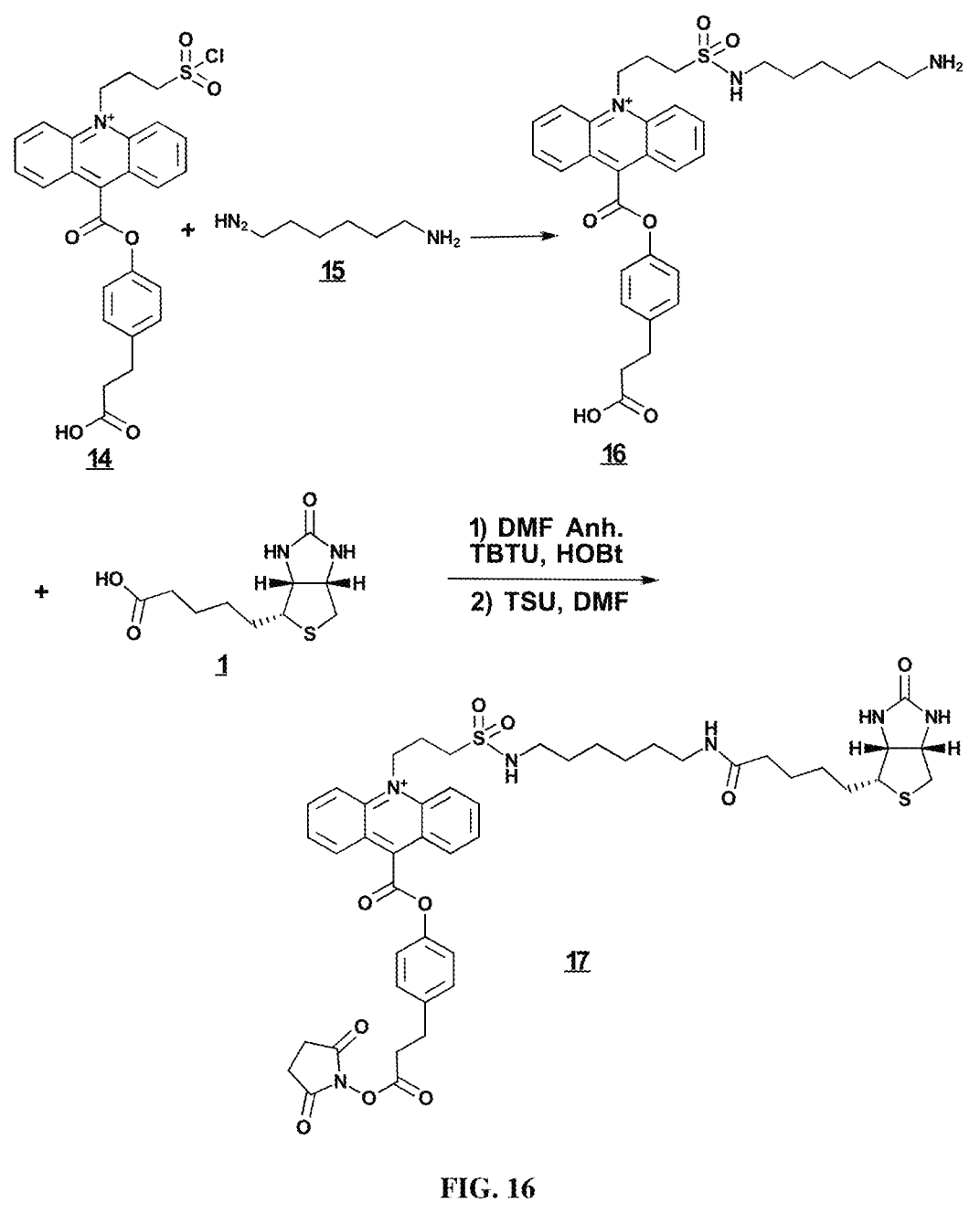

Compound 9 is designed and synthesized as shown in FIG. 14. Compound 9, can be used as a probe intermediate for coupling to a free amino group of an amine-linker, which can be incorporated into a nucleic acid sequence or other targeting moiety. The resulted probe is ready for hybridization and isolation or a rare target molecule, such as a rare gene target. Compound 17 is synthesized per the synthesis route, shown in FIG. 15 and FIG. 16. FIG. 15 shows an exemplary synthetic step in which biotin is quarternized to 10-nitrogen position of the dye. FIG. 16 shows an exemplary synthetic step in which a quaternary N-10-Biotinyl Dye NHS Ester (compound 17) is synthesized; such a compound can be used to prepare a segregating probe useful for sample preparation of rare genes present in specimen and plasma.

Synthesis of 4'-propionylcarboxyphenyl-10-N-sulfo-pronyl-dye-9-carboxylate-N-succinimidyl ester a) Synthesis of Hydroxyphenyl-4-benzyl Propionate 3-(4-Hydroxyphenyl)propionic Acid (10 g, 60 mmole) was dissolved in a 60 mL solution of 1 M potassium hydroxide. Water was removed in vacuo and the dried residue dissolved in 42.5 mL of ethyl alcohol, 2.5 mL of methyl alcohol, 2.5 mL of 2-propyl alcohol and 2.5 mL of water. 7.2 mL of benzyl bromide (60 mmole) was added dropwise to the solution after which the solution was heated to reflux for 3 hours. The solution was dried in vacuo and the syrup dissolved in a mixture of 100 mL of ether and 100 mL of a saturated sodium bicarbonate solution. The mixture was transferred to a separatory funnel and a second mixture of 100 mL of ether and 100 mL of a saturated sodium bicarbonate solution was added to the reaction flask. The mixtures were combined and an additional 100 mL of ethyl acetate added. The aqueous phase was removed and the ethyl acetate layer washed twice with separate 200 mL of a saturated sodium bicarbonate solution. The organic phase was dried over anhydrous magnesium sulfate, filtered, and the solvent removed in vacuo. The extent of the reaction was determined by TLC (7:3 hexane/EtOAc) on an alumina silica plate visualized by UV. The product was collected as pale yellow oil. Yield: 12.79 g (49.9 mmole, 83.17%), $H^1$-NMR results confirmed the resulting compound to be the desired product.

b) Synthesis of 4'-propionylcarboxyphenyl dye-9-carboxylate

A dye-9-carboxylic acid (as described in U.S. Pat. No. 5,521,103) (1.43 g, 6.4 mmol) in pyridine (30 mL) was cooled in an ice-bath under nitrogen atmosphere and treated with tosyl chloride (2.64 g, 12.8 mmole, 2 equivalents), after 10 minutes of stirring followed by hydroxyphenyl-4-benzyl propionate (1.64 g, 6.4 mmole, 1 equivalent). The reaction mixture was warmed to room temperature. The resulting mixture was continued stirring at room temperature, under nitrogen atmosphere. After 1 hour, an additional of 2 equivalents of tosyl chloride was added along with 0.5 equivalent of hydroxyphenyl-4-benzyl propionate and 15 mL of pyridine. The mixture was stirred for 24 hours at room temperature. An additional portion of hydroxy-phenyl-4-benzyl propionate and 15 mL of pyridine is added, and stirring continued for 24 hours. The solvent was then removed under reduced pressure and the residue was dissolved in dichlormethane 100 mL, and was washed with saturated aqueous sodium chloride solution 100 mL×2, and saturated aqueous sodium bicarbonate solution 100 mL×2. The solvent extract was then dried over magnesium sulfate, filtered and evaporated to dryness. The resulting residue was puri-fied by flash chromatography on 700 mL of dried silica gel using 5% ethyl acetate, 25% chloroform 70% hexanes. The $H^1$-NMR was analyzed to confirm the product, which presented as a light yellow powder.

c) Synthesis of 4'-propionylcarboxyphenyl-10-N-sulfopropanyl-dye-9-carboxylate The dye ester from above (20 mg, 38.4 μmoles), 1,3-propane sulfone (0.28 g, 2.29 mmoles) and sodium bicarbonate (32 mg, 384 μmoles) were mixed in a 10 mL round bottom flask and heated in an oil-bath at 120° C. under a nitrogen atmosphere. After 4 hours, the reaction was cooled to room temperature and diluted with ethyl acetate (10 mL). The suspension was soni-cated until the gummy solid was dispersed into the solvent to give a reddish-yellow precipitate. This pre-cipitate was collected by filtration and rinsed with ethyl acetate. It was then dissolved in methanol and filtered. HPLC analysis of the filtrate using a $C_{18}$ column (Phenomenex™ 4.6 mm×30 cm) and a 30 minute gradient of 10→70% MeCN in water (each solvent with 0.05% trifluoroacetic acid) showed product elut-ing at 23 minutes with ~10% starting material eluting at 31 minutes. The methanol solution was evaporated to dryness to give 42 mg of crude product which was stirred in 2 mL of 30% HBr/AcOH at room tempera-ture. Ether (30 mL) was added after 6 hours to precipi-tate the product, which was collected by filtration and rinsed with ether. The product was dissolved in metha-nol (40 mL) and analyzed by HPLC as described above. The product was found to elute at 15.9 minutes with no starting material. Evaporation of the methanol filtrate afforded an oily solid, which was redissolved in metha-nol (2-3 mL) and diluted with ethyl acetate (20 mL). Evaporation of the solvent yielded a yellow solid. Yield=34 mg. A portion of this material was dissolved in DMF (2-3 mL) and purified by preparative HPLC using a 30 mm×30 cm $C_{18}$ column. The HPLC fraction, containing product was frozen at −80° C. and, lyophilized to dryness to give a bright yellow powder. MALDI-TOF MS 555.7 obs. (553.6 calc.).

Synthesis of 4'-propionylcarboxyphenyl-2-aminocarboxybiotinyl-10-N-sulfopronyl-dye-9-carboxylate-N-succinimidyl ester a) Synthesis of Bromobenzene-4-biotinylcarboxylamide

4-Bromoaniline (2 g, 11.6 mmole), biotin (2.83 g, 11.6 mmole), O-(Benzotriazol-1-yl)-N,N,N',N'-tetramethyluronium tetrafluoroborate (TBTU, 743 g, 23.2 mmole, 2 equivalents), 1-hydroxybenzotriazole hydrate (HOBt, 3.12 g, 23.2 mmole, 2 equivalents) were mixed in 60 mL of anhydrous DMF. To the mixture was added N-ethylmorpholine (2.96 mL, 23.2 mmole, 2 equivalents), and stirred at room temperature under nitrogen atmosphere for 4 hours. The reaction solution was followed by TLC (solvent $CH_2Cl_2$:MeOH; 9:1). The crude product was concentrated under high vacuum pump, and purified on column chromatography using 70 mL of dried silica gel, and 2 L of solvent ($CH_2Cl_2$: MeOH; 9:1).

Synthesis of 4'-propionylcarboxyphenyl-2-aminocarboxyhexylaminocarboxy-biotinyl-10-N-sulfopronyl-dye-9-carboxylate-N-succinimidyl ester a) Synthesis of Bromobenzene-4-carboxylamidohexylamine

4-Bromoaniline (2 g, 11.6 mmole), 6-amino-caproic acid (1.52 g, 11.6 mmole), O-(Benzotriazol-1-yl)-N,N,N', N'-tetramethyluronium tetrafluoroborate (TB TU, 743 g, 23.2 mmole, 2 equivalents), 1-hydroxybenzotriazole hydrate (HOBt, 3.12 g, 23.2 mmole, 2 equivalents) were mixed in 40 mL of anhydrous DMF. To the mixture was added N-ethylmorpholine (2.96 mL, 23.2 mmole, 2 equivalents), and stirred at room temperature under nitrogen atmosphere for 4 hours. The reaction solution was followed by TLC (solvent $CH_2Cl_2$: MeOH; 9:1). The crude product was concentrated under high vacuum pump, and purified on column chromatography using 50 mL of dried silica gel, and 2 L of solvent ($CH_2Cl_2$:MeOH; 9:1).

Exemplary Synthesis B

Figure 17:
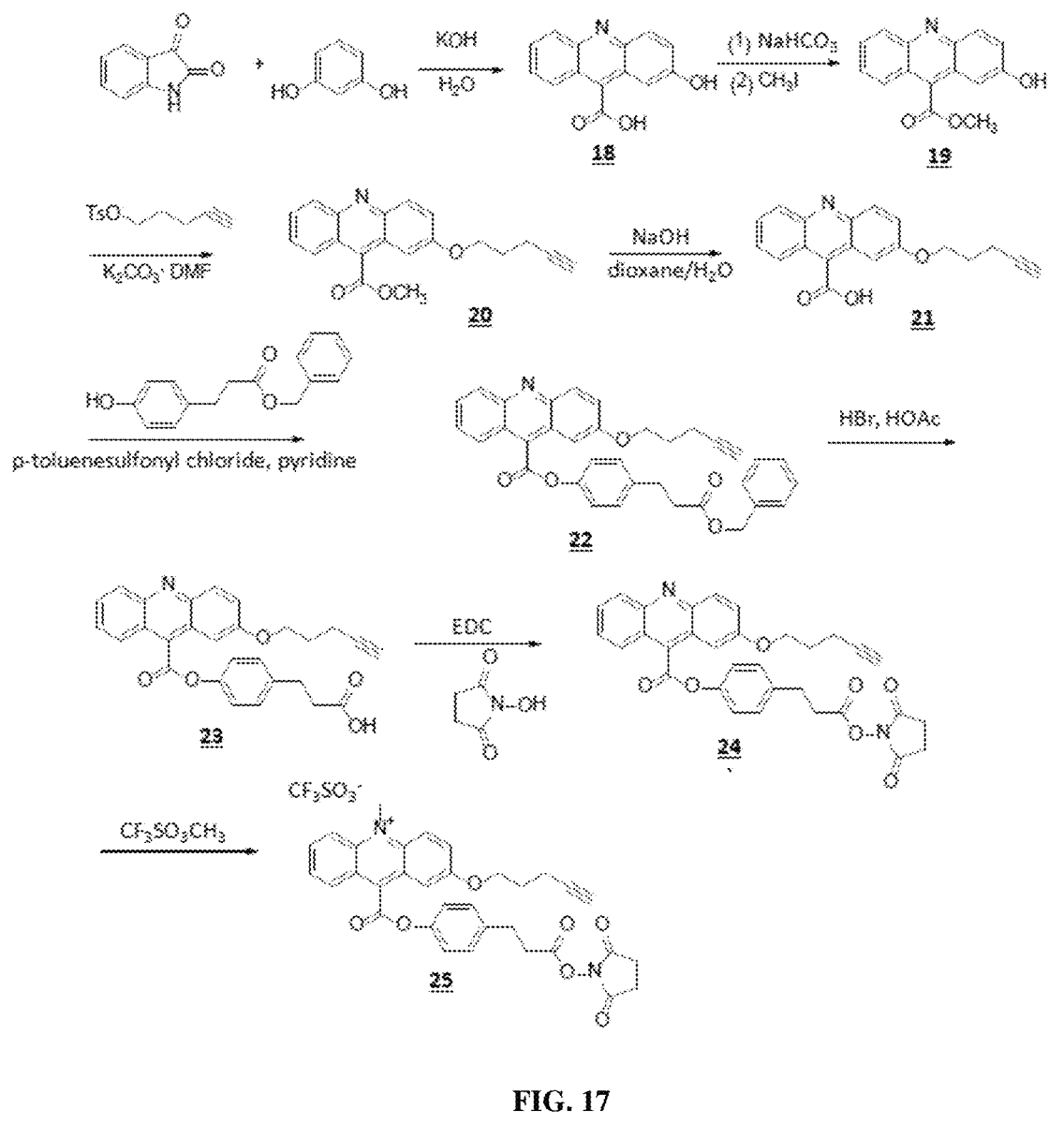

A general synthetic scheme for a segregating probe intermediate having the structure of compound 25 is shown in FIG. 17. The intermediate includes a N-hydroxysuccinimide group suitable for coupling to nucleophilic groups (e.g. an amine of an amine modified polynucleotide, a lysine ε-amine, an N-terminal amine of a polypeptide, etc.) and a Click chemistry compatible group. HPLC-MS analyses were performed on Waters™ HPLC 2790 with Waters micromass ZQ 4000™ (Model MAA050) as mass detector and Waters 2487 UV™ as detector. The separation column used was a Phenomemex™ OOB-4605-E0 (5u-XB-C18-100A, 50×4.6 mm) column. The mobile phase consists eluent A (water, 0.05% TFA) and eluent B (CH3CN, 0.05% TFA), and the elution proceeded at 1 mL/min. The initial conditions were 90% A for 1 min, then 90% A to 10% A linearly decreased within 5 min, then from 10% A to 90% A within 1 min. The total run time is 7 minutes.

Synthesis of compound 18: Compound 1 was prepared according to published procedures (see EP0322926A2) (4 g, yield: 32%).

Synthesis of compound 19: Compound 18 (4 g) was mixed with 100 ml of 10% $NaHCO_3$ aqueous solution and stir for 2 hours. The reaction mixture was filtered to give an orange solid. After drying in air, the solid was mixed with 30 ml of DMSO, methyl iodide was added, and the mixture was stirred for 3 hours. The reaction mixture was then poured into 500 ml of water. The solid was filtered and then purified by column chromatography on silica gel using hexane/EtOAC as eluting solvent. 1 g product (compound 19) was obtained (yield: 24%). MS: 254.56 (M+H).

Synthesis of compound 20: Compound 19 (1 g) was dissolved in 15 ml of DMF, and $K_2CO_3$ (1.1 g) was added, followed by pent-4-yn-1-yl 4-methylbenzenesulfonate (1.1 g). The mixture was stirred for 1 hour at room temperature and then 4 hours at 80° C. Water was added and the product was extracted with EtOAc and purified by column chromatography on silica gel using hexane/EtOAc as eluting solvents. A yellow solid was obtained (0.4 g, yield 30%). MS: 320.25 (M+H).

Synthesis of compound 21: Compound 20 (330 mg) was mixed with 5 ml of 1N NaOH aqueous solution and 5 ml of dioxane. The mixture was heated to reflux for 2 hours. After cooling to room temperature the dioxane was removed using a rotavapor. The aqueous solution was acidified with 6N HCl aqueous solution to pH 1. The yellow precipitate was filtered and dried under vacuum. 310 mg of product was obtained (yield: ~100%). MS: 306.34 (M+H).

Synthesis of compound 22: To a mixture of compound 21 (220 mg) in 5 ml of dry pyridine was added p-toluenesulfonyl chloride (1.37 g) followed by stirring for 2 hours. Benzyl 3-(4-hydroxyphenyl)propanoate (204 mg) was added and the mixture was stirred at room temperature overnight. Solvent was removed using a rotavapor and the residue was taken up in 100 ml of EtOAc, washed with 1N HCl aqueous solution and brine, dried over $Na_2SO_4$, then purified by column chromatography on silica gel using hexane and EtOAc as eluting solvents. A brown solid was obtained (310 mg, yield 43%). MS: 544.58 (M+H).

Synthesis of compound 23: Compound 22 (240 mg) was mixed with 3 mL of acetic acid and 3 ml of 30% HBR aqueous solution. The mixture was stirred at room temperature overnight. Water was added and the mixture extracted with DCM. Solvent was removed using a rotavapor and the remaining solution dried under vacuum to give a brown solid (200 mg, yield ~100). MS: 454.60 (M+H).

Synthesis of compound 24: Compound 23 (110 mg) was mixed with 5 mL of dichloromethane. N-hydroxy-succimide (30 mg) and EDC (110 mg) were added and the mixture stirred at room temperature overnight. Water was added and the resulting mixture extracted with EtOAc, then purified by column chromatography on silica gel using hexane and EtOAc as eluting solvents. A yellow solid was obtained (55 mg, yield 41%). MS: 551.52 (M+H).

Synthesis of compound 25: Compound 24 (55 mg) was dissolved in 2 mL of dry DCM. Methyl trifluoromethanesulfonate (1 ml) was added and the mixture was stirred at room temperature under argon overnight. Solvent was removed using a rotavapor and the crude product was purified by column chromatography on silica gel using dichloromethane and acetonitrile as eluting solvent. 12 mg of final product was obtained as yellow solid (yield: 17%). MS: 565.99 (M-$CF_3SO_3$).

Exemplary Segregation of KRAS Mutant Sequence from Mixtures

A segregating probe was prepared by reacting 1 nmole of aminomodified polynucleotide including a sequence complementary to a KRAS G12A mutation (SEQ ID NO 2)

reconstituted in 1 μl of TE buffer, pH 8.0, mixed with 2 μl of nuclease-free water, 1 μl of 1M HEPES (pH 8.0), 4 μl of DMSO, and 2 μl of compound 25 at a concentration sufficient to provide a molar excess, in a final labeling reaction volume of 10 μl in a capped vial. Following light vortexing and a brief spin to settle the liquid, the reaction mixture was incubated in a 37° C. heat block for 20 minutes. To improve the labeling efficiency, an additional 3 μl of the compound 25 solution was added to the reaction mixture, with an additional 1.5 μl of nuclease-free water, and 0.5 μl of 1 M HEPES buffer at pH 8.0 for a total reaction volume of 15 μl in the capped vial. Following light vortexing and a brief spin to settle the liquid, the labeling reaction mixture was further incubated in a 37° C. heat block for 20 minutes.

The NHS-ester/Amine polynucleotide labeling reaction was stopped by quenching through the addition of 5 μl of 0.125 M lysine (containing free primary amines) in 1 M HEPES, pH 7.5 to 8.5, with 50% DMSO. The 20 μl mixture was lightly vortexed and briefly spun, then incubated at room temperature for 5 minutes. The resulting acridinium-labeled polynucleotide was then precipitated by adding 30 μl of 3M NaOAc (ph 5.0), 245 μl of nuclease-free water, and 5 μl of molecular biology-grade glycogen. Following a light vortex and a brief spin, 640 μl of pure ethanol was then added to the reaction mixture, and thoroughly vortexed. To encourage precipitation, the reaction mixture was incubated in a −20° C. freezer, then spun in a microcentrifuge at 17,000 rpm to pellet the glycogen and the labeled polynucleotide. The supernatant was then removed and the pellet air-dried for 15 minutes using HEPA-filtered room temperature air. The pellet was then used for the subsequent Click Chemistry reaction. In some embodiments the precipitation procedure can be performed without the inclusion of additional glycogen in the second precipitation.

The acridinium-labeled polynucleotides were next labeled with biotin-PEGS-azide linkers (p/n BP-21510, Broadpharm™, USA) in a Click-Chemistry reaction. Following the NHS/Amine labeling steps, the dry T pellet was rehydrated with 22.5 μl of nuclease-free water. The rehydrated pellet was then mixed with μl of 2 M triethylammonium acetate buffer, pH 7.0, followed by the addition of 50 μl DMSO. This solution was then vortexed to ensure even mixing prior to the addition of 7.5 ul of biotin-PEGS-azide (10 mM in DMSO). The reaction was vortexed again, then 10 μl of freshly prepared 5 mM ascorbic acid solution was added to the mixture and vortexed. The reaction mixture was then degassed with a flow of nitrogen gas for 30 seconds, mixed with 5 μl of 10 mM Copper II-TBTA catalyst in 55% DMSO and briefly vortexed. The vial was degassed with nitrogen gas once again, after which the cap was closed. When significant precipitation of azide was observed, the reaction was heated for 3 minutes at 80° C. and vortexed. After vortexing, the clear reaction mixture was kept at ambient temperature overnight. The following day, the 100 μl reaction mixture containing the completed segregating probe was mixed with 400 μl of acetone, mixed thoroughly, and placed in a −20° C. freezer for 20 minutes. To pellet the precipitate, the vial was spun in a microcentrifuge at 10,000 rpm for 10 minutes. The acetone supernatant was removed, and 1 ml of fresh acetone was added to the pellet, vortexed, and placed in a −20° C. freezer for 20 minutes. The solution was then centrifuged at 10,000 rpm for 10 minutes to create the final pellet containing the segregating probe. The supernatant was discarded, and the pellet (containing the segregating probe product) was air dried for 15 minutes at room temperature. The pellet was then solubilized in 1 ml of PSB, forming the stock solution of the segregating probe. Working solutions of the resulting segregating probe were prepared by diluting the stock solution 1:9 in PSB. The stock solution and the working solutions of the segregating probe were stored at −20° C. between uses.

As noted above, the exemplary segregating probe was designed to selectively enrich KRAS G12A mutations (TACGCCAGCAGC, SEQ ID NO 2) in presence of an excess of the KRAS wild type (WT) sequence (TACGC-CACCAGC, SEQ ID NO 1). In order to design PCR primers for the amplification of KRAS exon 2, the reference sequences were obtained from NCBI (NCBI accession number NG_007524) and imported into Geneious™ sequence alignment editor program (version 9.1.8). The process of primer design was conducted manually, and no automated software packages were used. The primer set used for KRAS amplification were: (i) PCR amplification 1, KRAS_Forward 5'GCCTGCTGAAAATGACTGAA3' (10,526 to 10,545 bp, SEQ ID NO 3) and KRAS_Reverse 5'GAATGGTCCTGCACCAGTAA3' (SEQ ID NO 4), resulting in a 166 bp product; and (ii) PCR Amplification 2, KRAS_Forward 5'GCCTGCTGAAAATGACTGAA3' (nucleotide positions 10,526 to 10,545 bp, SEQ ID NO 5) and KRAS_Reverse 5'GAATGGTCCTGCACCAGTAA3' (nucleotide positions 10,672 to 10,691, SEQ ID NO 6), also generating a fragment of 166 bp. These primers pair allowed the amplification of 166 base pairs, comprising nucleotide positions 10,526 to 10,691 based on NCBI accession number NG_007524 for the human KRAS gene. Buffers suitable for use in an enrichment reaction as described below include Probe Storage Buffer 1 (100 mM Sodium Acetate, 0.1% sodium dodecyl sulfate, pH 5.0), Probe Storage Buffer 2 (100 mM Sodium Acetate, pH 5.0), Annealing Buffer 1 (200 mM Succinic Acid, 0.8 M Lithium Chloride, 10% Lithium Lauryl Sulfate, 2 mM EDTA, 2 mM EGTA, pH adjusted to 5.1 using Lithium Hydroxide, mixed 1:1 with Probe Storage Buffer 1), Annealing Buffer 2 (200 mM Succinic Acid, 0.8 M Lithium Chloride, 2 mM EDTA, 2 mM EGTA, pH adjusted to 5.1 using Lithium Hydroxide, mixed 1:1 with Probe Storage Buffer 2), and Cleaving Reagent (150 mM Sodium tetraborate decahydrate, pH adjusted to 8.5 with concentrated Nitric Acid, with Triton X-100 at 5.68 ml per liter).

Mutated human KRAS genomic DNA, extracted from engineered SW48 human cell lines, was obtained from Horizon Discovery™ (United Kingdom, p/n HD265). Each genomic DNA preparation contained 50% of one KRAS mutation in either the G12 or G13 codon, according manufacturer's description. The percentage of each KRAS mutation was adjusted by serially diluting the mutated DNA with wildtype human DNA from Promega™ (USA, p/n G1521) to create complex samples with differing KRAS mutation levels. The final DNA concentration was adjusted to 10 ng of DNA per micoliter in molecular biology grade TE buffer, pH 8.0. The freshly diluted DNA samples were briefly kept at room temperature prior to being mixed with the PCR Master Mix and primers.

KRAS exon 2 amplification using PCR as follows. The prepared genomic DNA was amplified by PCR using Power SYBR Green Master Mix™ (Life Technologies™, USA, p/n 4367659). The total reaction mixture volume of 25 μL contained the following: PCR reaction mix (10 μL), 10 μM primers (0.46 μL each), and genomic DNA template (10 μL, containing 10 ng of DNA). PCR conditions for the first amplification were as follows: Activation of Taq Polymerase at 95° C. for 10 min, 40 amplification cycles of denaturation at 95° C. for 30 seconds, annealing at 57° C. for 30 seconds, and extension at 72° C. for 15 seconds. For the second PCR (i.e. after selective enrichment using the segregating probe, see below), the PCR product eluted from Dynabead™ streptavidin magnetic beads (Life Technologies™, USA, p/n 11205D) in 25 µL of TE buffer, pH 8.0, and mixed with 1.15 µL of each primer (at 10 µM) added to 25 µl of fresh Power SYBR Green Master Mix. PCR conditions for the second amplification were identical to those of the first PCR amplification.

Enrichment of mutant amplicons from the first PCR step (as described above) using a segregating probe of the inventive concept was performed as follows. Preheat a shaking heating block, designed for 12 mm tubes, to 95° C. Into a 12 mm×75 mm round bottom polypropylene tube with 100 µl annealing buffer, add 1 µl of a segregating probe working solution. Amplicons from the first PCR (20 µl) are then added, mixed, and the tube transferred to the preheated heating block. After incubating at 95° C. for 1 minute, the reset heating block is reset to 60° C. When the heating block reaches 60° C., the reaction mixture is incubated for an additional 10 minutes at 60° C. 300 µl of a cleaving reagent (see above) is added to the reaction mixture, mixed, and incubate for 60 minutes at 60° C. The tube is then removed from the heating block, and 10 µl of Dynabeads™ M-280 Streptavidin was added to each tube to capture biotinylated species (including intact segregating probe complexed with amplicons including the KRAS G12A mutation). The tube was incubated for 10 minutes at ambient temperature while shaking. The tube was then placed on compatible magnetic rack until the solution was cleared of the magnetic beads. The supernatant, containing a preponderance of cleaved segregating probes, was removed. The remaining magnetic beads, retaining a preponderance of uncleaved segregating probes and their respective targets, were then washed twice with 700 µl of annealing buffer (sans detergent). After the final wash, 100 µl of annealing buffer (sans detergent) was added to the pellet, mixed thoroughly, and the entire mixture transferred to a 96 well PCR plates. The magnetic beads with uncleaved segregating probe and bound target were then exposed to a compatible magnetic rack, and the annealing buffer supernatant was removed. To disassociate the bound PCR amplicons from the magnetic bead bound segregating probes the beads were mixed with 25 ul of TE buffer, pH 8.0 and placed on a 96w plate compatible magnetic rack. The clarified (magnetic bead-free) DNA sample was then removed in approximately 25 µl of the clarified TE buffer, and used as the DNA sample for the second PCR reaction (see above).

The 166 bp PCR product of KRAS Exon 2 was sequenced by Sanger sequencing on an ABI 3730x1 DNA Analyzer™ using POP-7™ 50 cm capillaries. The products of the first PCR or the second PCR (rare species enriched) were used directly as samples, without purification. The sequencing primer (SEQ ID NO 4), was diluted to 5 µM in TE buffer, pH 8.0. The full sequencing reaction was prepared in a 96 well plate, each well containing 8 µl of unpurified PCR amplicons, 1 µl of primer, and 0.5 µL of BigDye Terminator™ v3.1 cycle sequencing kit (Applied Biosystems™). Sequencing chromatograms from .ab1 files were generated using Applied Biosystems Sequencing Analysis Software™ version 6, base called by KB™ version 1.4.1.8, and observed using Variant Analysis™ software (Thermo-Fisher™, USA). All genotypes were verified by manual observation of fluorescence peaks.

Figure 18A:
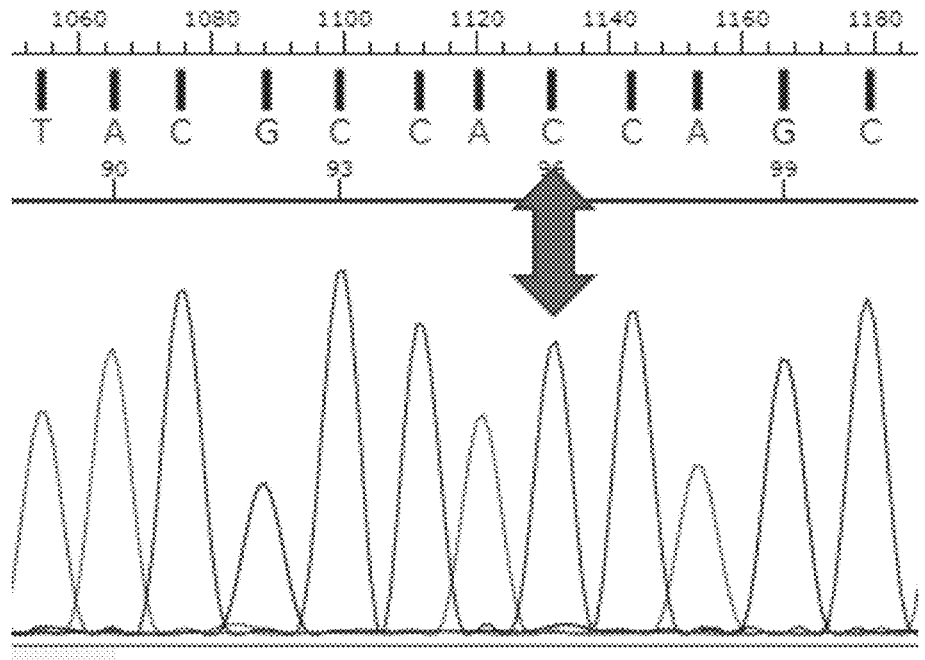
FIGS. 18A and 18B.
Figure 18B:
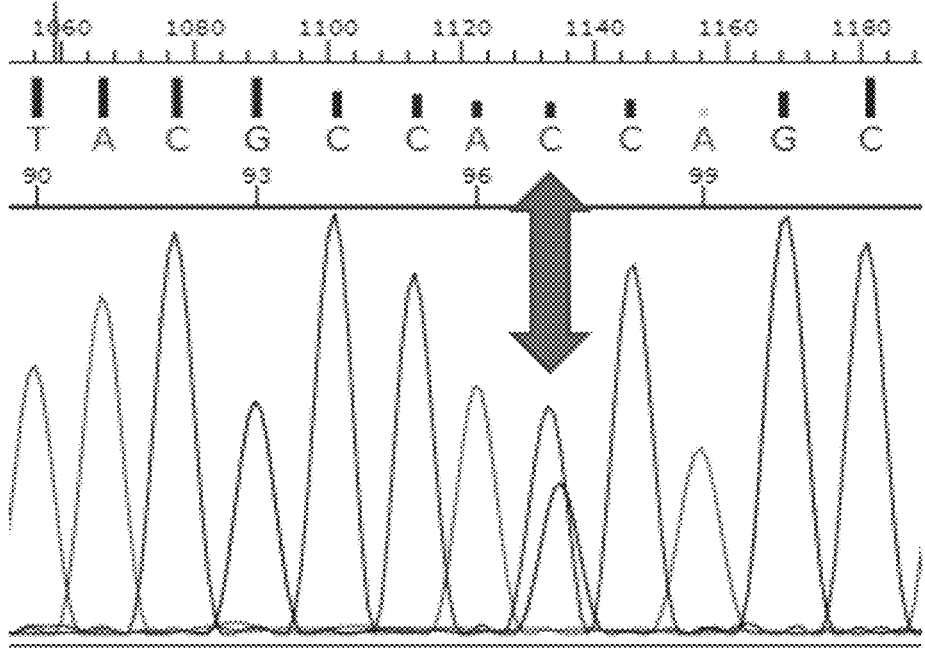

An exemplary Sanger reaction result from an untreated preparation of genomic DNA containing KRAS WT sequence (SEQ ID NO 1) and also containing 5% genomic DNA carrying the KRAS G12A mutation (SEQ ID NO. 2)

is shown in FIG. 18A. The presence of the KRAS G12A sequence (SEQ ID NO 2) is not evident in the untreated sample. FIG. 18B shows an exemplary Sanger reaction result from the same mixture shown in FIG. 18A following enrichment with a segregating probe of the inventive concept designed to enrich KRAS G12A mutation (SEQ ID NO 2) content (i.e. complementary to SEQ ID NO 2). A high degree of enrichment in the KRAS G12A mutation sequence (SEQ ID NO 2) is evident following enrichment using a segregating probe of the inventive concept.

Figure 19A:
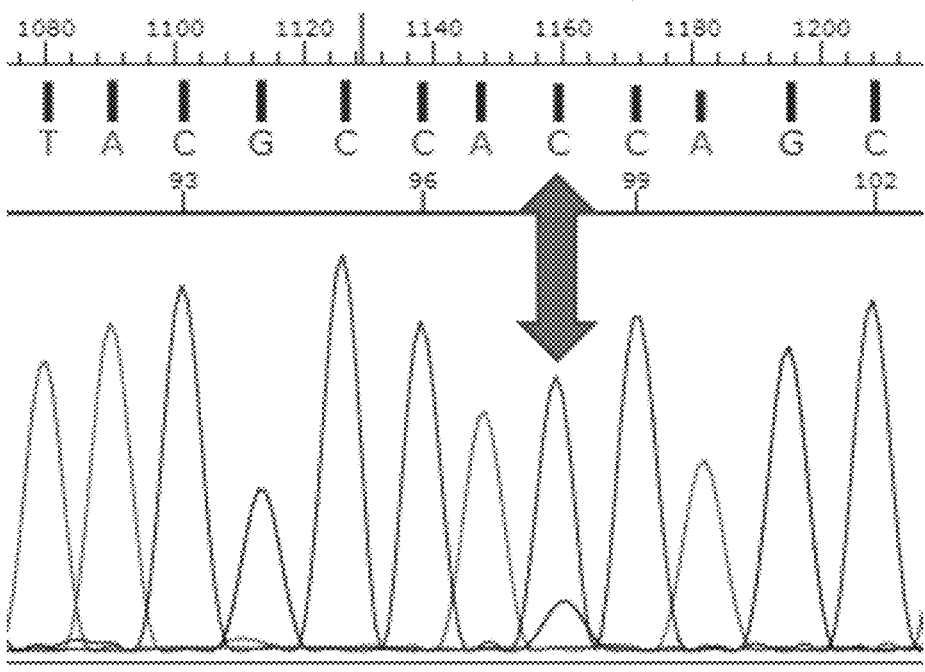
FIGS. 19A and 19B.
Figure 19B:
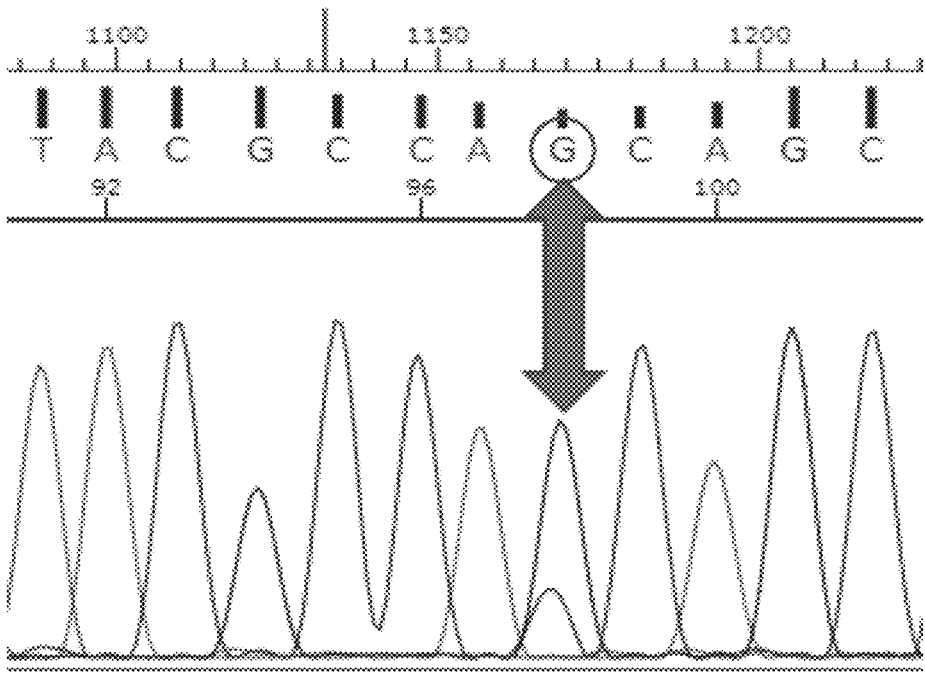

A similar result is found for an preparations containing 20% genomic DNA that includes the KRAS G12A mutation (SEQ ID NO. 2), exemplary results for which are shown in FIG. 19A. The presence of the KRAS G12A sequence (SEQ ID NO 2) is observable as a very minor peak. FIG. 19B shows an exemplary Sanger sequencing reaction result from the same mixture shown in FIG. 19A following enrichment with a segregating probe of the inventive concept designed to enrich KRAS G12A mutation (SEQ ID NO 2) content. A high degree of enrichment in the KRAS G12A mutation sequence (SEQ ID NO 2), sufficient to provide direct identification of the mutant sequence, is evident following enrichment using a segregating probe of the inventive concept.

Figure 20A:
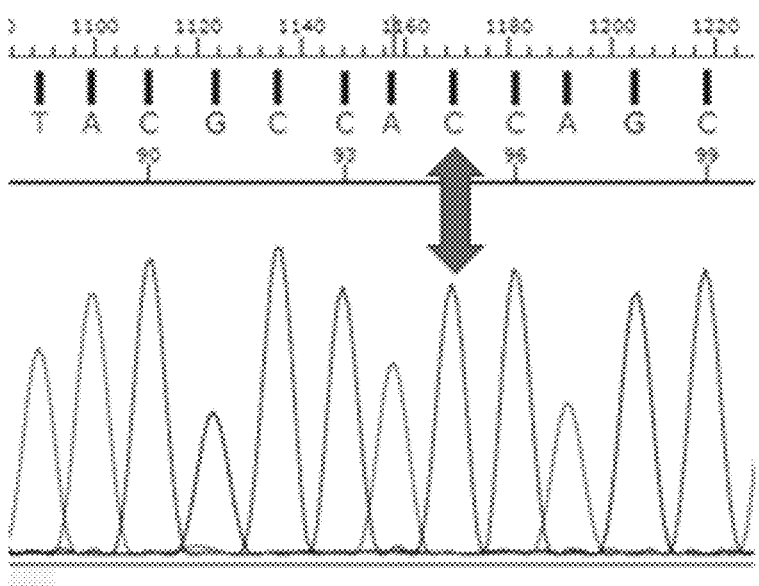
FIGS. 20A and 20B.
Figure 20B:
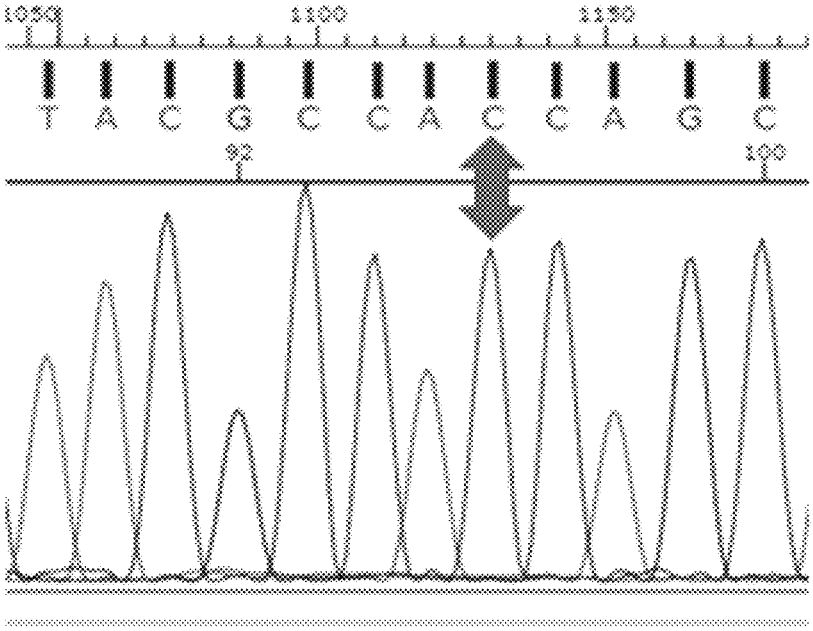

Exemplary results for Sanger sequencing of an untreated preparation containing only genomic DNA carrying the KRAS WT sequence (SEQ ID NO 1) is shown in FIG. 20A. FIG. 20B shows an exemplary Sanger sequencing reaction result from the same mixture shown in FIG. 20A following enrichment with a segregating probe of the inventive concept designed to enrich KRAS G12A mutation (SEQ ID NO 2) content. No evidence of the KRAS G12A mutation (SEQ ID NO 2) is present, showing that enrichment of this sequence is template-dependent and is not an artifact of the segregation probe process.

While Sanger sequencing was utilized in these examples, it should be appreciated that a wide variety of nucleic acid detection and characterization technologies can be utilized. Suitable technologies include amplification-based technologies (e.g. PCR. RT-PCR, rolling circle amplification, linear amplification, etc.) and/or hybridization-based technologies (e.g. blotting, hybridization to bead arrays, hybridization to microarrays, etc.). The results shown are exemplary, and Inventors believe that further improvements will be realized through optimization of probe design, methodology (for example, additional processing of enriched samples with the segregating probe), and/or characterization methodology.

The examples of a mismatch-sensitive cleavable bond provided in the examples are based on single base mismatches, but can be envisioned to operate on a multitude of mutation types, genetic or epigenetic, including methylated DNA, inverted bases, small and large insertions, small and large deletions, and fusion gene junctions. Furthermore, the cleavable probes are predicted to work within a variety of nucleic acid probe compositions, including RNA probes, probes with synthetic nucleotide variants, or probes with altered backbones (LNA, PNA, XNA), and are structurally compatible with a variety of probe designs, including Molecular Beacons, Scorpions, Taqman probes, Fret probes, where the labels may be placed between bases, off of nucleic acid bases, or at 5' and 3' ends of the nucleic acid probe.

While the exemplary molecule governing the mismatch-sensitive base-cleavage of the ester bond is based on acridinium, the Inventors believe that similarly structured small molecules linked to chemically labile bonds can also act to shield a base-, acid-, photochemically- or enzymatically sensitive bond in a nucleic acid probe (e.g., fluorescein, minor groove binders, etc), resulting in a labeled and an unlabeled probe-target population.

While the experimental examples demonstrate the utility of a mismatch-sensitive cleavable linker when labeled with a biotin linker, there inventors envision additional utilities based on the match/mismatch use of different labels conferring a multitude of properties on the nucleic acid species retaining the labels after cleavage. Examples include fluorescent labels, quenchers, attachment moieties, enzymes, enzyme inhibitors, enzyme blockers, non-target nucleic acid polymers, minor and major groove binders, charged labels, mass-changing labels, dielectrohoretic labels, photocleavable labels, electrically responsive labels, or labels that sterically hinder the recognition of nucleic acid complexes by proteins or antibodies.

While the above examples are directed to nucleic acids, it should be appreciated that segregating probes can be directed to other molecules (e.g. proteins, carbohydrates, lipids, small molecules, etc.), molecular complexes, and/or cells of interest by suitable selection of the targeting moiety and characterization method. For example, enrichment of rare proteins can be accomplished by using specific single chain antibodies as targeting groups whereas enrichment of rare carbohydrates can be accomplished by using specific lectins as targeting groups. In such embodiments suitable detection technologies can include blots, immunoassays, and/or mass spectrometry. Similarly, specific cell population can be enriched by selecting specific binding partners for cell surface receptors as targeting groups. In such embodiments suitable detection technologies include microscopy and/or fluorescence activated cell sorting.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for segregating a first polynucleotide from a mixture of polynucleotides, comprising:

obtaining a segregating probe comprising a targeting polynucleotide moiety that is complementary to the first polynucleotide and coupled to a capture tag by a linker interposed between the targeting polynucleotide moiety and the capture tag, wherein the linker comprises a cleavage site comprising a covalent scissile bond comprising an ester bond coupled to a first position on an acridinium group of a modified acridinium dye, and a protective moiety comprising the modified acridinium dye, such that the ester bond is protected from hydrolysis when the first polynucleotide is part of a polynucleotide duplex with the targeting polynucleotide, wherein the cleavage site is interposed between the targeting polynucleotide moiety and the capture tag, wherein the capture tag is coupled to a second position on the acridinium group;

contacting the segregating probe with a sample comprising a mixture of the first polynucleotide and a related second polynucleotide to form a first reaction mixture, wherein the second polynucleotide is present in at least a 5-fold molar excess over the first polynucleotide, and wherein the targeting polynucleotide moiety is partially complementary to the second polynucleotide;

permitting a first complex comprising the segregating probe and the first polynucleotide and a plurality of second complexes comprising the segregating probe and the second polynucleotide to form in the first reaction mixture, wherein the protective moiety of the first complex is positioned to prevent cleavage of the scissile bond of the first complex on exposure to a cleavage reagent and wherein the protective moieties of the second complexes are not positioned to prevent cleavage of the scissile bonds of the second complexes on exposure to the cleavage reagent;

selectively cleaving the second complexes, thereby separating the second polynucleotides of the second complexes from the capture tags of the second complexes, by adding the cleavage reagent to the first reaction mixture to form a second reaction mixture comprising the first complex and cleaved second complexes;

contacting the second reaction mixture with a capture species that selectively binds the capture tag to form a third complex comprising the capture species and the first complex;

applying a wash buffer to separate the second polynucleotides from the third complex; and releasing the first polynucleotide from the third complex.

2. The method of claim 1, wherein the ester bond is selected from the group consisting of a carbonyl ester and a sulfonamide ester.

3. The method of claim 1, wherein the capture tag is selected from the group consisting of biotin, iminobiotin, digoxigenin, a polypeptide, polyhistidine, an antibody, an antibody fragment, and an antibody derivative.

4. The method of claim 1, wherein the capture species further comprises at least one of the group consisting of a particle, a magnetically responsive particle, a membrane, a well of a microwell plate, an interior surface of a pipette tip or vial, and a filter.

5. The method of claim 1, wherein the step of selective cleavage comprises treatment with a base.

6. A reagent, comprising:

a targeting polynucleotide moiety configured to form a complex with a first polynucleotide and a second polynucleotide;

a capture tag coupled to the targeting moiety via a linker interposed between the targeting polynucleotide moiety and the capture tag, wherein the linker comprises a cleavage site comprising a covalent scissile bond comprising an ester bond coupled to a first position on an acridinium group of a modified acridinium dye, wherein the capture tag is coupled to a second position on the acridinium group, such that the targeting polynucleotide moiety is released from the capture tag on scission of the scissile bond; and a protective group comprising a modified acridinium dye, wherein the protective group is positioned to provide a reduced rate of cleavage of the scissile bond when the segregating probe is part of a first complex comprising the segregating probe and the first polynucleotide, relative to the rated of cleavage of the scissile bond in a second complex comprising the segregating probe and the second polynucleotide.

7. The reagent of claim 6, wherein the ester bond is selected from the group consisting of a carbonyl ester or a sulfonamide ester.

8. The reagent of claim 6, wherein the capture tag is selected from the group consisting of biotin, iminobiotin, digoxigenin, a polypeptide, polyhistidine, an antibody, an antibody fragment, and an antibody derivative, and is selected to form a third complex with a capture species.

9. An intermediate for preparation of a segregating probe, comprising:
  a capture tag;
  a cleavage site comprising a covalent scissile bond comprising an ester bond coupled to a first position of a modified acridinium dye;
  a protective group comprising the modified acridinium dye, wherein the modified acridinium dye is positioned such that the ester bond is protected from hydrolysis when the targeting polynucleotide is part of a polynucleotide duplex with a target nucleic acid sequence; and
  a reactive group coupled to a second position of the acridinium group and selected to form a covalent bond with a targeting polynucleotide moiety, wherein th cleavage site is interposed between the capture tag and the reactive group.

10. The intermediate of claim 9, wherein the ester bond is selected from the group consisting of a carbonyl ester or a sulfonamide ester.

11. The intermediate of claim 9, wherein the capture tag is selected from the group consisting of biotin, iminobiotin, digoxigenin, a polypeptide, polyhistidine, an antibody, an antibody fragment, and an antibody derivative, and is selected to form a third complex with a capture species.

12. A method for segregating a first polynucleotide from a mixture of polynucleotides, comprising:
  contacting a segregating probe comprising a targeting polynucleotide moiety that is complementary to the first polynucleotide and coupled to a capture tag by a linker interposed between the targeting polynucleotide moiety and the capture tag, wherein the linker comprises a cleavage site comprising a covalent scissile bond comprising an ester bond of a modified acridinium dye, and a protective moiety, wherein the cleavage site is interposed between the targeting polynucleotide moiety and the capture moiety, and wherein the ester bond is selected from the group consisting of a carbonyl ester and a sulfonamide ester, with a sample comprising a mixture of the first polynucleotide and a related second polynucleotide to form a first reaction mixture, wherein the second polynucleotide is present in at least a 5-fold molar excess over the first polynucleotide, and wherein the targeting polynucleotide moiety is partially complementary to the second polynucleotide;

permitting a first complex comprising the segregating probe and the first polynucleotide and a plurality of second complexes comprising the segregating probe and the second polynucleotide to form in the first reaction mixture, wherein the protective moiety of the first complex is positioned to prevent cleavage of the scissile bond of the first complex on exposure to a cleavage reagent and wherein the protective moieties of the second complexes are not positioned to prevent cleavage of the scissile bonds of the second complexes on exposure to the cleavage reagent;

selectively cleaving the second complexes, thereby separating the second polynucleotides of the second complexes from the capture tags of the second complexes, by adding the cleavage reagent to the first reaction mixture to form a second reaction mixture comprising the first complex and cleaved second complexes;

contacting the second reaction mixture with a capture species that selectively binds the capture tag to form a third complex comprising the capture species and the first complex;

applying a wash buffer to separate the second polynucleotides from the third complex; and releasing the first polynucleotide from the third complex.

13. A reagent, comprising:
  a targeting polynucleotide moiety configured to form a complex with a first polynucleotide and a second polynucleotide;
  a capture tag coupled to the targeting moiety via a linker interposed between the targeting polynucleotide moiety and the capture tag, wherein the linker comprises a cleavage site comprising a covalent scissile bond comprising an ester bond of a modified acridinium dye, wherein the ester bond is selected from the group consisting of a carbonyl ester and a sulfonamide ester, such that the targeting polynucleotide moiety is released from the capture tag on scission of the scissile bond;
  and
  a protective group,
  wherein the protective group is positioned to provide a reduced rate of cleavage of the scissile bond in a first complex comprising the segregating probe and the first polynucleotide relative to the rated of cleavage of the scissile bond in a second complex comprising the segregating probe and the second polynucleotide.

14. An intermediate for preparation of a segregating probe, comprising:
  a reactive group selected to form a covalent bond with a targeting polynucleotide moiety;
  a capture tag;
  a cleavage site comprising a covalent scissile bond comprising an ester bond of a modified acridinium dye, wherein the ester bond is selected from the group consisting of a carbonyl ester and a sulfonamide ester, wherein the cleavage site is interposed between the capture tag and the reactive group; and
  a protective group.

* * * * *

SEQUENCE LISTING

```
<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: KRAS wild type sequence

<400> SEQUENCE: 1
tacgccacca gc                                                          12

<210> SEQ ID NO 2
<211> LENGTH: 12
<212> TYPE: DNA
<213> ORGANISM: Artificial Sequence
<220> FEATURE:
<223> OTHER INFORMATION: KRAS G12A mutation sequence

<400> SEQUENCE: 2
tacgccagca gc                                                          12

<210> SEQ ID NO 3
<211> LENGTH: 20
<212> TYPE: DNA
<213> ORGANISM: Artificial Sequence
<220> FEATURE:
<223> OTHER INFORMATION: KRAS_Forward primer, 10,526 to 10,545 bp

<400> SEQUENCE: 3
gcctgctgaa aatgactgaa                                                  20

<210> SEQ ID NO 4
<211> LENGTH: 20
<212> TYPE: DNA
<213> ORGANISM: Artificial Sequence
<220> FEATURE:
<223> OTHER INFORMATION: KRAS_Reverse primer

<400> SEQUENCE: 4
```

-continued

```
gaatggtcct gcaccagtaa                                            20

<210> SEQ ID NO 5
<211> LENGTH: 20
<212> TYPE: DNA
<213> ORGANISM: Artificial Sequence
<220> FEATURE:
<223> OTHER INFORMATION: KRAS_Foward primer, 10,526 to 10,545 bp

<400> SEQUENCE: 5
gcctgctgaa aatgactgaa                                            20

<210> SEQ ID NO 6
<211> LENGTH: 20
<212> TYPE: DNA
<213> ORGANISM: Artificial Sequence
<220> FEATURE:
<223> OTHER INFORMATION: KRAS_Reverse primer, 10,672 to 10,691

<400> SEQUENCE: 6
gaatggtcct gcaccagtaa                                            20
```